(12) United States Patent
Prausnitz et al.

(10) Patent No.: US 7,344,499 B1
(45) Date of Patent: Mar. 18, 2008

(54) MICRONEEDLE DEVICE FOR EXTRACTION AND SENSING OF BODILY FLUIDS

(75) Inventors: Mark R. Prausnitz, Decatur, GA (US);
Mark G. Allen, Atlanta, GA (US);
Inder-Jeet Gujral, Cambridge, MA (US)

(73) Assignee: Georgia Tech Research Corporation, Atlanta, GA (US)

( * ) Notice: Subject to any disclaimer, the term of this patent is extended or adjusted under 35 U.S.C. 154(b) by 0 days.

(21) Appl. No.: 09/453,109

(22) Filed: Dec. 2, 1999

Related U.S. Application Data

(63) Continuation-in-part of application No. 09/316,229, filed on May 21, 1999, now Pat. No. 6,334,856, which is a continuation-in-part of application No. 09/095,221, filed on Jun. 10, 1998, now Pat. No. 6,503,231.

(60) Provisional application No. 60/146,200, filed on Jul. 29, 1999.

(51) Int. Cl.
*A61B 5/00* (2006.01)
(52) U.S. Cl. ............ 600/309; 600/310; 600/347; 600/573
(58) Field of Classification Search ........ 600/309–310, 600/316, 345, 347–348, 362, 369, 365, 573–576; 422/68.1; 604/191, 190
See application file for complete search history.

(56) References Cited

U.S. PATENT DOCUMENTS 2,893,392 A  7/1959  Wagner et al.

(Continued)

FOREIGN PATENT DOCUMENTS

EP    0497620    8/1992

(Continued)

OTHER PUBLICATIONS

"Single-crystal whiskers," *Biophotonics Int'l* p. 64 (Nov./Dec. 1996).

(Continued)

*Primary Examiner*—Eric F Winakur
(74) *Attorney, Agent, or Firm*—Ropes and Gray LLP

(57) ABSTRACT

Microneedle devices are provided for controlled sampling of biological fluids in a minimally-invasive, painless, and convenient manner. The microneedle devices permit in vivo sensing or withdrawal of biological fluids from the body, particularly from or through the skin or other tissue barriers, with minimal or no damage, pain, or irritation to the tissue. The microneedle device includes one or more microneedles, preferably in a three-dimensional array, a substrate to which the microneedles are connected, and at least one collection chamber and/or sensor in communication with the microneedles. Preferred embodiments further include a means for inducing biological fluid to be drawn through the microneedles and into the collection chamber for analysis. In a preferred embodiment, this induction is accomplished by use of a pressure gradient, which can be created for example by selectively increasing the interior volume of the collection chamber, which includes an elastic or movable portion engaged to a rigid base. Preferred biological fluids for withdrawal and/or sensing include blood, lymph, interstitial fluid, and intracellular fluid. Examples of analytes in the biological fluid to be measured include glucose, cholesterol, bilirubin, creatine, metabolic enzymes, hemoglobin, heparin, clotting factors, uric acid, carcinoembryonic antigen or other tumor antigens, reproductive hormones, oxygen, pH, alcohol, tobacco metabolites, and illegal drugs.

48 Claims, 9 Drawing Sheets

U.S. PATENT DOCUMENTS

| | | | |
|---|---|---|---|
| 3,034,507 A | 5/1962 | McConnell et al. | |
| 3,086,530 A | 4/1963 | Groom | |
| 3,123,212 A | 3/1964 | Taylor et al. | |
| 3,136,314 A | 6/1964 | Kravitz | |
| RE25,637 E | 9/1964 | Kravitz et al. | |
| 3,221,739 A | 12/1965 | Rosenthal | |
| 3,221,740 A | 12/1965 | Rosenthal | |
| 3,556,080 A | 1/1971 | Hein | |
| 3,596,660 A | 8/1971 | Melone | |
| 3,675,766 A | 7/1972 | Rosenthal | |
| 3,918,449 A | 11/1975 | Pistor | |
| 3,964,482 A | 6/1976 | Gerstel et al. | |
| 4,109,655 A | 8/1978 | Chacornac | |
| 4,159,659 A | 7/1979 | Nightingale | |
| 4,222,392 A | 9/1980 | Brennan | |
| 4,320,758 A | 3/1982 | Eckenhoff et al. | |
| 4,664,651 A * | 5/1987 | Weinshenker et al. | 604/115 |
| 4,671,288 A * | 6/1987 | Gough | 600/347 |
| 4,703,761 A * | 11/1987 | Rathbone et al. | 600/576 |
| 4,771,660 A | 9/1988 | Yacowitz | |
| 4,798,582 A | 1/1989 | Sarath et al. | |
| 4,921,475 A | 5/1990 | Sibalis | |
| 4,969,468 A | 11/1990 | Byers et al. | |
| 5,035,711 A | 7/1991 | Aoki et al. | |
| 5,054,339 A | 10/1991 | Yacowitz | |
| 5,138,220 A | 8/1992 | Kirkpatrick | |
| 5,250,023 A | 10/1993 | Lee et al. | |
| 5,279,544 A | 1/1994 | Gross et al. | |
| 5,279,552 A | 1/1994 | Magnet | |
| 5,335,670 A | 8/1994 | Fishman | |
| 5,364,374 A | 11/1994 | Morrison et al. | |
| 5,383,512 A | 1/1995 | Jarvis | |
| 5,401,242 A | 3/1995 | Yacowitz | |
| 5,457,041 A | 10/1995 | Ginaven et al. | |
| 5,527,288 A | 6/1996 | Gross et al. | |
| 5,582,184 A | 12/1996 | Erickson et al. | |
| 5,591,139 A | 1/1997 | Lin et al. | |
| 5,605,662 A | 2/1997 | Heller et al. | |
| 5,611,806 A | 3/1997 | Jang | |
| 5,611,809 A | 3/1997 | Marshall et al. | |
| 5,611,942 A | 3/1997 | Mitsui et al. | |
| 5,618,295 A | 4/1997 | Min | |
| 5,632,957 A | 5/1997 | Heller et al. | |
| 5,658,515 A | 8/1997 | Lee et al. | |
| 5,697,901 A | 12/1997 | Eriksson | |
| 5,722,397 A * | 3/1998 | Eppstein | 600/345 |
| 5,801,057 A | 9/1998 | Smart et al. | |
| 5,807,375 A * | 9/1998 | Gross et al. | 604/890.1 |
| 5,843,114 A | 12/1998 | Jang | |
| 5,848,991 A * | 12/1998 | Gross et al. | 604/140 |
| 5,852,495 A | 12/1998 | Parce | |
| 5,858,188 A | 1/1999 | Soane et al. | |
| 5,865,786 A | 2/1999 | Sibalis et al. | |
| 5,876,675 A | 3/1999 | Kennedy | |
| 5,879,326 A | 3/1999 | Godshall et al. | |
| 5,883,211 A | 3/1999 | Sassi et al. | |
| 6,080,116 A * | 6/2000 | Erickson et al. | 600/573 |
| 6,132,755 A | 10/2000 | Eicher et al. | |
| 6,312,612 B1 * | 11/2001 | Sherman et al. | 216/2 |
| 6,334,856 B1 * | 1/2002 | Allen et al. | 604/191 |
| 6,503,231 B1 * | 1/2003 | Prausnitz et al. | 604/272 |
| 2001/0053891 A1 * | 12/2001 | Ackley | 604/191 |

FOREIGN PATENT DOCUMENTS

| | | |
|---|---|---|
| EP | 0 652 600 A1 | 5/1995 |
| JP | 7-132119 A | 5/1995 |
| JP | 132119 | 5/1995 |
| JP | 7-196314 A | 8/1995 |
| WO | WO 93/17754 A1 | 9/1993 |
| WO | WO 96/372546 A1 | 11/1996 |
| WO | WO 96/40365 A1 | 12/1996 |
| WO | WO 96/41236 A1 | 12/1996 |
| WO | WO 97/07734 A1 | 3/1997 |
| WO | 98/00194 | 1/1998 |
| WO | WO 98/00193 A1 | 1/1998 |
| WO | WO 98/28037 A1 | 7/1998 |
| WO | 00/48669 | 8/2000 |

OTHER PUBLICATIONS

"101 Uses for Tiny Tubules," *Science* 247 (1990).
Amsden & Goosen, "Transdermal Delivery of Peptide and Protein Drugs: an Overview," *AIChE Journal* 41 (8):1972-1997 (1995).
Bronaugh & Maibach, Percutaneous Absorption, Mechanisms—Methodology—Drug Delivery (Marcel Dekker, New York 1989).
Brumlik & Martin, "Template Synthesis of Metal Microtubules," *J. Am. Chem. Soc.* 113:3174-3175 (1991).
Despont, et al., "High-Aspect-Ratio, Ultrathick, Negative-Tone Near-UV Photoresist for MEMS," *Proc. of IEEE 10th Annual International Workshop on MEMS*, Nagoya, Japan, pp. 518-522 (Jan. 26-30, 1997).
Edell, et al., "Factors Influencing the Biocompatibility of Insertable Silicon Microshafts in Cerebral Cortex," *IEEE Transactions on Biomedical Engineering* 39(6):635-43 (1992).
Frazier & Allen, "Metallic Microstructures Fabricated Using Photosensitive Polyimide Electroplanting Molds," *Journal of Microelectromechanical Systems* 2:87-97 (1993).
Frazier, et al., "Two dimensional metallic microelectrode arrays for extracellular stimulation and recording of neurons", *IEEE Proceedings of the Micro Electro Mechanical Systems Conference*, pp. 195-200 (1993).
Hadgraft & Guy, eds., *Transdermal Drug Delivery: Developmental Issues and Research Initiatives* (Marcel Dekker, New York 1989).
Haga, et al., "Transdermal iontophoretic delivery of insulin using a photoetched microdevice," *J. Controlled Release* 43:139-49 (1997).
Hashmi, et al., "Genetic Transformation of Nematodes Using Arrays of Micromechanical Piercing Structures," *BioTechniques* 19(5):766-70 (1995).
Henry, et al., "Microfabricated microneedles: A novel method to increase transdermal drug delivery" *J. Pharm. Sci.* 87:922-25 (1998).
Henry, et al., "Micromachined Needles for the Transdermal Delivery of Drugs," *Micro Electro Mechanical Systems*, Heidelberg, Germany, pp. 494-98 (Jan. 26-29, 1998).
Hoffert, "Transcutaneous methods get under the skin," *The Scientist* 12 (1998).
Jaeger, *Introduction to Microelectronic Fabrication* (Addison-Wesley Publishing Co., Reading MA 1988).
Jansen, et al., "Black Silicon Method IV: The Fabrication of Three-Dimensional Structures in Silicon with High Aspect Ratios for Scanning Probe Microscopy and Other Applications," *IEEE Proceedings of Micro Electro Mechanical Systems Conference*, pp. 88-93 (1995).
Laermer, et al., "Bosch Deep Silicon Etching: Improving Uniformity and Etch Rate for Advanced MEMS Applications," *Micro Electro Mechanical Systems*, Orlando, Fl, USA, (Jan. 17-21, 1999);.
Langer, "Drug Delivery and Targeting," *Nature* 392:5-10 (1998).
Lehmann, "Porous Silicon—A New Material for MEMS", *IEEE Proceedings of the Micro Electro Mechanical Systems Conference*, pp. 1-6 (1996).
Lin, et al., "Silicon Processed Microneedles," *The 7th International Conference on Solid-State Sensors and Actuators* 237-240 (1993).
Martin, et al., "Template Synthesis of Organic Microtubules," *J. Am. Chem. Soc.* 112:8976-8977 (1990).
Najafi, et al., "Strength Characterization of Silicon Microprobes in Neurophysiological Tissues," *IEEE Transcriptions on Biomedical Engineering* 37(5): 474-481 (1990).
Prausnitz, "Reversible Skin Permeabilization for Transdermal Delivery of Macromolecules," *Critical Reviews in Therapeutic Drug Carrier Systems* 37(5): 474-481 (1990).
*Proceedings of the IEEE Micro Electro Mechanical Systems Conference 1987-1998*; Rai-Choudhury, ed., *Handbook of*

*Microlithography, Micromachining & Microfabrication* (SPIE Optical Engineering Press, Bellingham, WA 1997).

Quan, "Plasma etch yields microneedle arrays," *Electronic Engineering Times* 63:63-64 (1998).

Reiss, "Glucose- and Blood-Monitoring Systems Vie for Top Spot," *Biophotonics Int'l*, pp. 43-45 (1997).

Runyan, et al., *Semiconductor Integrated Circuit Processing Technology*, Addison-Wesley Publishing Co.:Reading, MA, 1990.

Schift, et al., "Fabrication of replicated high precision insert elements for micro-optical bench arrangements" *Proc. SPIE—International Soc. Optical Engineer* 3513:122-134 (1998).

Talbot & Pisano, "Polymolding: Two Wafer Polysilicon Micromolding of Closed-Flow Passages for Microneedles and Microfluidic Devices," *Solid-State Sensor and Actuator Workshop Hilton Head Island, South Carolina*, Jun. 8-11 266-268 (1988).

Trimmer, et al., "Injection of DNA into Plant and Animal Tissues with Micromechanical Piercing Structures," *IEEE Proceedings of Micro Electro Mechanical Systems Conference*, pp. 111-15 (1995).

Weber, et al., "Micromolding—a powerful tool for the large scale production of precise microstructures," *Proc. SPIE—International Soc. Optical Engineer* 2879:156-167 (1996).

Zuska, "Microtechnology Opens Doors to the Universe of Small Space," *Medical Device and Diagnostic Industry*, p. 131 (1997).

U.S. Appl. No. 09/095,221, filed Jun. 10, 1998, Prausnitz et al.

U.S. Appl. No. 09/316,229, filed May 21, 1999, Allen et al.

U.S. Appl. No. 09/452,979, filed Dec. 02, 1999, Prausnitz et al.

* cited by examiner

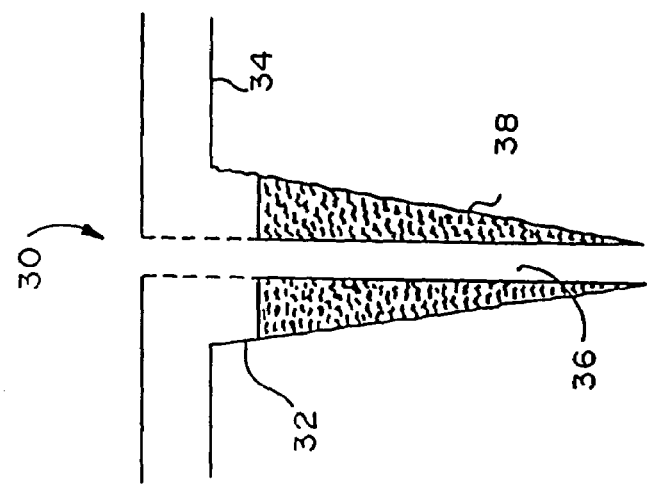
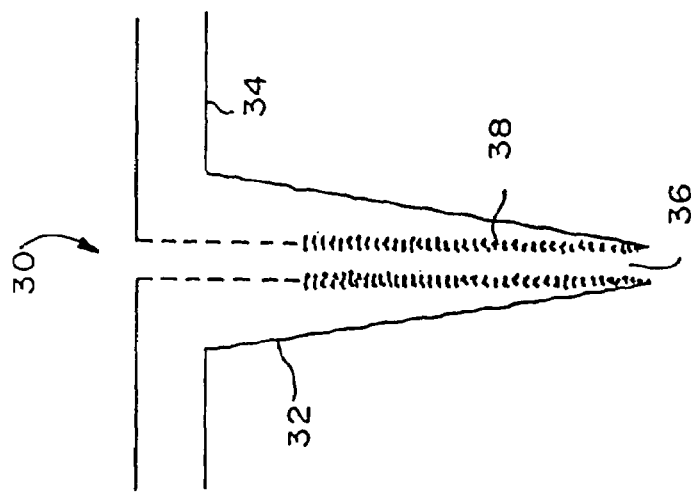
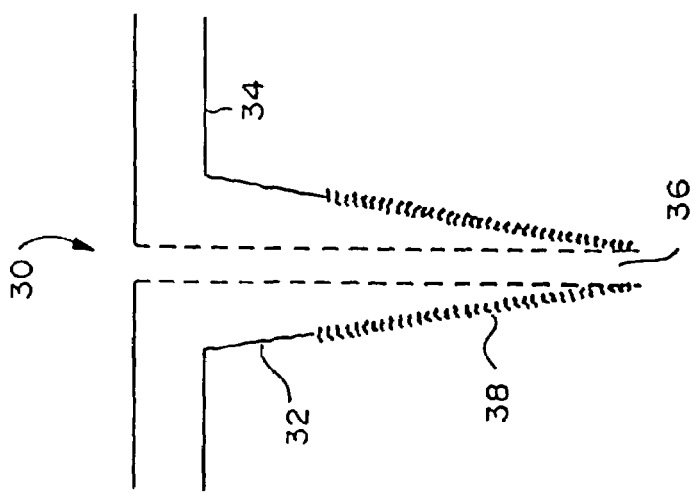

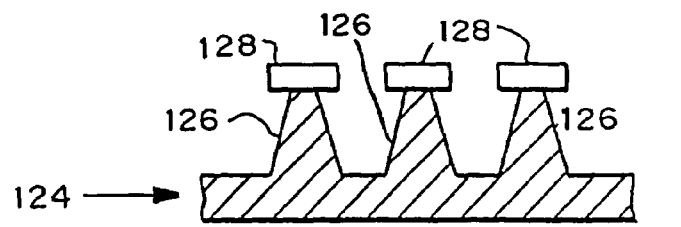
FIG. 7A
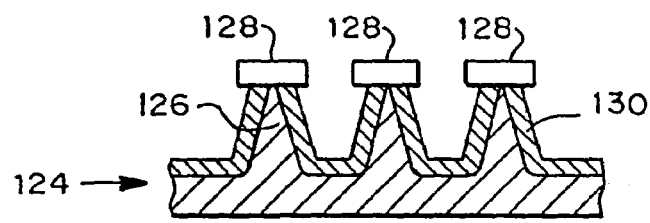
FIG. 7B
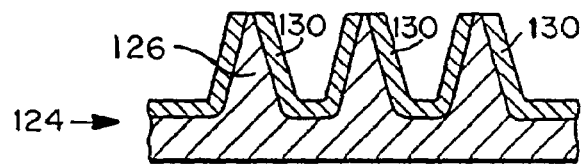
FIG. 7C
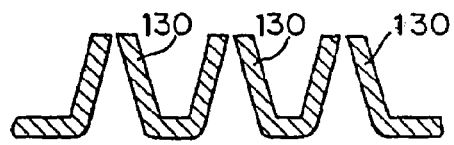
FIG. 7D
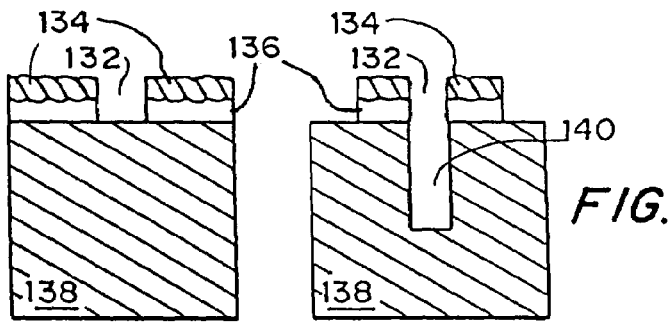
FIG. 8A
FIG. 8C
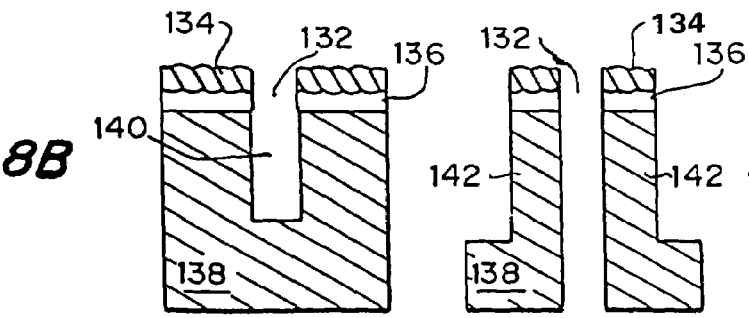
FIG. 8B
FIG. 8D

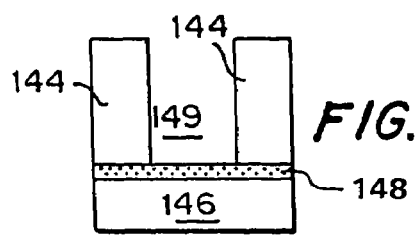
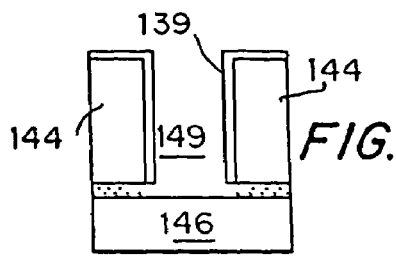
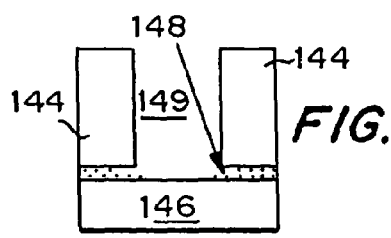
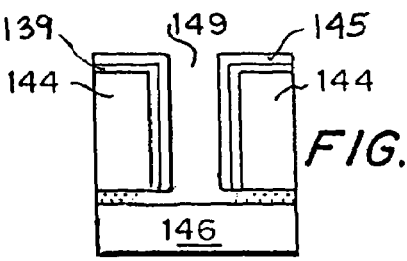
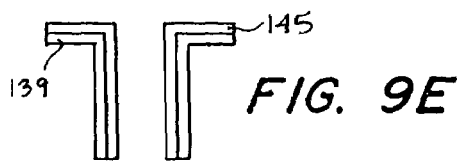
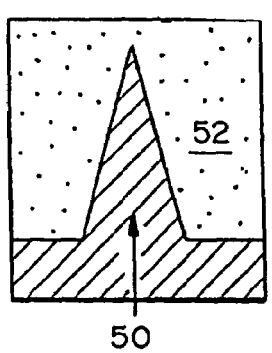
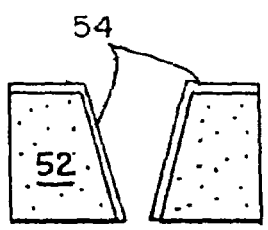
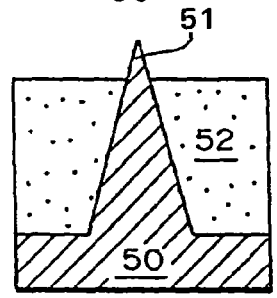
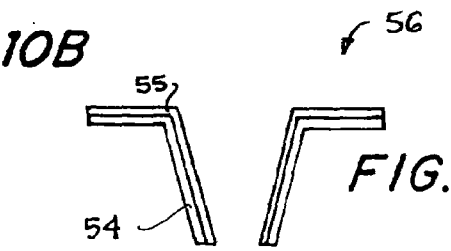

MICRONEEDLE DEVICE FOR EXTRACTION AND SENSING OF BODILY FLUIDS

CROSS-REFERENCE TO RELATED APPLICATIONS

This application is a continuation-in-part of U.S. patent application Ser. No. 09/316,229, now U.S. Pat. No. 6,334,856, filed May 21, 1999, which is a continuation-in-part of U.S. patent application Ser. No. 09/095,221, now U.S. Pat. No. 6,503,231, filed Jun. 10, 1998. This application claims the benefit of the filing date of U.S. provisional application Ser. No. 60/146,200, filed Jul. 29, 1999.

STATEMENT REGARDING FEDERALLY SPONSORED RESEARCH

This invention was made with government support under Contract Number BES-9813321 awarded by the U.S. National Science Foundation. The government has certain rights in the invention.

BACKGROUND OF THE INVENTION

This invention is generally in the field of devices for the withdrawal and sensing of biological fluids, such as in the analysis of blood glucose levels.

The extraction of analytes through the skin is critical to diabetic patients, who typically must measure blood glucose several times per day in order to optimize insulin treatment and thereby reduce the severe long-term complications of the disease. Currently, diabetics do this by pricking the highly vascularized fingertips with a lancet to perforate the skin, then milking the skin with manual pressure to produce a drop of blood, which is then assayed for glucose using a disposable diagnostic strip and a meter into which the strip fits. This method of glucose measurement has the major disadvantage that it is painful, so diabetics do not like to obtain a glucose measurement as often as is medically indicated. It would therefore be highly useful to be able to obtain a sample of blood, lymph, or interstitial fluid more quickly, using an easier procedure, and relatively noninvasively. It also would be advantageous to be able to repeatedly or continually extract analyte transdermally over a period of time.

Another common technique for withdrawal of bodily fluids, such as for diagnostic purposes, is the use of a needle, such as those used with standard syringes or catheters. While effective for this purpose, needles are invasive and generally cause pain; local damage to the skin at the site of insertion; and bleeding, which can increase the risk of disease transmission. Needle techniques also generally require administration by one trained in its use, and are not preferred for frequent routine use due to the vascular damage caused by repeated punctures. Some proposed alternatives to the needle require the use of (1) lasers or heat to create a hole in the skin, which is inconvenient, expensive, or undesirable for repeated use; (2) electric fields or ultrasound, which also is inconvenient and expensive; or (3) chemical or biological penetration enhancing agents, which can be irritating to the tissue and undesirable for repeated use.

It is therefore an object of the present invention to provide a device for controlled sampling of biological fluids in a minimally-invasive, painless, and convenient manner.

It is another object of the present invention to provide a device for sensing of biological fluids in a minimally-invasive, painless, and convenient manner.

SUMMARY OF THE INVENTION

Microneedle devices for controlled sampling of biological fluids in a minimally-invasive, painless, and convenient manner, are provided. The microneedle devices permit in vivo sensing or withdrawal of biological fluids from the body, particularly from or through the skin or other tissue barriers, with minimal or no damage, pain, or irritation to the tissue.

The microneedle device includes one or more microneedles, preferably in a three-dimensional array, a substrate to which the microneedles are connected, and at least one collection chamber and/or sensor in communication with the microneedles. Preferred embodiments further include a means for inducing biological fluid to be drawn through the microneedles and into the collection chamber for analysis. In a preferred embodiment, this induction is accomplished by use of a pressure gradient, which can be created for example by selectively increasing the interior volume of the collection chamber, which includes an elastic or movable portion engaged to a rigid base.

In a preferred embodiment, the microneedle device further comprises means for transduction, storage, transmission, and display of measured values. The microneedle device also preferably includes means for securing the device to a biological barrier during withdrawal or sensing.

Preferred biological fluids for withdrawal and/or sensing include blood, lymph, interstitial fluid, and intracellular fluid. Examples of analytes in the biological fluid to be measured include glucose, cholesterol, bilirubin, creatine, metabolic enzymes, hemoglobin, heparin, clotting factors, uric acid, carcinoembryonic antigen or other tumor antigens, reproductive hormones, oxygen, pH, alcohol, tobacco metabolites, and illegal drugs.

BRIEF DESCRIPTION OF THE FIGURES

FIGS. 3a-c are cross-sectional views of preferred embodiments of a microneedle device in which a sensor is included on the external surface of a hollow needle (3a), on the internal bore surface of a hollow needle (3b), and within the pores of a porous, hollow needle (3c).

FIGS. 7a-d are side cross-sectional views illustrating a preferred method for making hollow microneedles.

FIGS. 8a-d are side cross-sectional views illustrating a preferred method for making hollow silicon microtubes.

FIGS. 9a-e are side cross-sectional views illustrating a preferred method for making hollow metal microtubes.

FIGS. 10a-d are side cross-sectional views illustrating a preferred method for making tapered metal microneedles.

DETAILED DESCRIPTION OF THE INVENTION

1. The Microneedle Device

Figure 1:
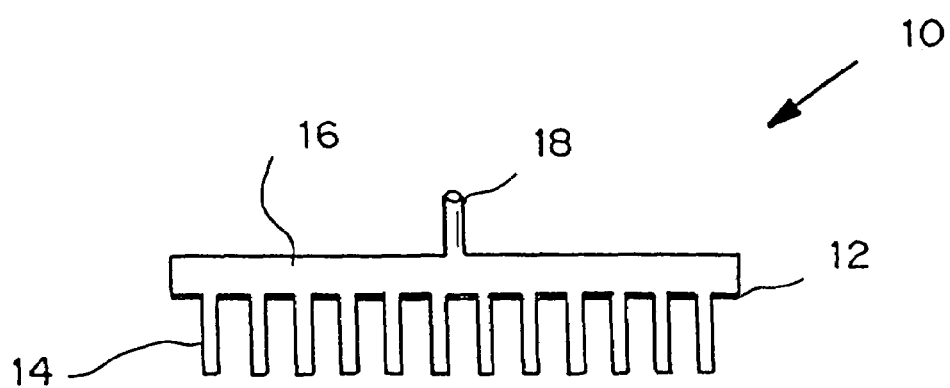
FIG. 1 is a cross-sectional view of a preferred embodiment of a microneedle device for fluid withdrawal.

The microneedle devices include at least three components: at least one, preferably more, microneedle(s), a substrate to which the base of the microneedle(s) is secured or integrated, and at least one fluid collection chamber and/or sensor that is selectably in communication with at least one microneedle. Typically, the microneedles are provided as a three-dimensional array, in contrast to a device with a single needle or row of needles. The microneedle device can be adapted to be a single-use, disposable device, or can be adapted to be fully or partially reusable.

a. Substrate

The substrate of the device can be constructed from a variety of materials, including metals, ceramics, semiconductors, organics, polymers, and composites. The substrate includes the base to which the microneedles are attached or integrally formed. A fluid collection chamber and/or sensor can be attached to the substrate or formed (e.g., as part of the substrate) to communicate directly with the base of the microneedles.

b. Microneedles

The microneedles function either as a conduit, a sensing element, or a combination thereof. Conduit microneedles can have a porous or hollow shaft. As used herein, the term "porous" means having pores or voids throughout at least a portion of the microneedle structure, sufficiently large and sufficiently interconnected to permit passage of fluid and/or solid materials through the microneedle. As used herein, the term "hollow" means having one or more substantially annular bores or channels through the interior of the microneedle structure, which have a diameter sufficiently large to permit passage of fluid and/or solid materials through the microneedle. The annular bores may extend throughout all or a portion of the needle in the direction of the tip to the base, extending parallel to the direction of the needle or branching or exiting at a side of the needle, as appropriate. A solid or porous microneedle can be hollow. One of skill in the art can select the appropriate porosity and/or bore features required for specific applications. For example, one can adjust the pore size or bore diameter to permit or regulate passage of the particular material to be transported through the microneedle device.

In one embodiment, one or more of the microneedles are coated (if solid, porous, or hollow) and/or at least partially filled (if porous or hollow) with a sensing or diffusion-modifying material.

The microneedles of the device can be constructed from a variety of materials, including metals, ceramics, semiconductors, organics, polymers, and composites. Preferred materials of construction include pharmaceutical grade stainless steel, gold, titanium, nickel, iron, tin, chromium, copper, palladium, platinum, alloys of these or other metals, silicon, silicon dioxide, and polymers. Representative biodegradable polymers include polymers of hydroxy acids such as lactic acid and glycolic acid polylactide, polyglycolide, polylactide-co-glycolide, and copolymers with PEG, polyanhydrides, poly(ortho)esters, polyurethanes, poly(butyric acid), poly(valeric acid), and poly(lactide-co-caprolactone). Representative non-biodegradable polymers include polycarbonate, polymethacrylic acid, ethylenevinyl acetate, polytetrafluoroethylene (TEFLON™), and polyesters.

The microneedles should have the mechanical strength to remain intact for sensing analyte and/or for serving as a conduit for the collection of biological fluid, while being inserted into the skin, while remaining in place for up to a number of days, and while being removed. In embodiments where the microneedles are formed of biodegradable polymers, the microneedle must remain intact at least long enough for the microneedle to serve its intended purpose (e.g., its conduit function). The microneedles should be sterilizable using standard methods, such as ethylene oxide treatment or gamma irradiation. The microneedles can have straight or tapered shafts. A hollow microneedle that has a substantially uniform diameter, which needle does not taper to a point, is referred to herein as a "microtube." As used herein, the term "microneedle" includes both microtubes and tapered needles unless otherwise indicated. In a preferred embodiment, the diameter of the microneedle is greatest at the base end of the microneedle and tapers to a point at the end distal the base. The microneedle can also be fabricated to have a shaft that includes both a straight (untapered) portion and a tapered portion.

The microneedles can be formed with shafts that have a circular cross-section in the perpendicular, or the cross-section can be non-circular. For example, the cross-section of the microneedle can be polygonal (e.g. star-shaped, square, triangular), oblong, or another shape. The shaft can have one or more bores. The cross-sectional dimensions typically are between about 1 μm and 500 μm, and preferably between 10 μm and 100 μm. The outer diameter is typically between about 10 μm and about 100 μm, and the inner diameter is typically between about 3 μm and about 80 μm.

The length of the microneedles typically is between about 10 μm and 1 mm, preferably between 100 μm and 500 μm, and more preferably between 150 μm and 350 μm. The length is selected for the particular application, accounting for both an inserted and uninserted portion. An array of microneedles can include a mixture of microneedles having, for example, various lengths, outer diameters, inner diameters, cross-sectional shapes, and spacings between the microneedles. Preferably, the microneedles are sized to avoid or minimize contact with nerve endings in the biological tissue, such as the dermis, thereby eliminating or reducing pain when the microneedles are inserted, for example into the skin.

The microneedles can be oriented perpendicular or at an angle to the substrate. Preferably, the microneedles are oriented perpendicular to the substrate to provide structural strength and to permit ease of insertion into the tissue. An array of microneedles can include a mixture of microneedle orientations, heights, spacings, or other parameters. This variation in an array can be useful, for example, if different microneedles are to provide different sensing or insertion functions.

In one embodiment, the microneedle has one or more holes (ports) or slits positioned on the sides of the shaft of a hollow microneedle having a blunt, open, or closed tip. This design may reduce blockage of the conduit, for example, due to tissue or cells when the microneedles are inserted.

In a preferred embodiment of the device, the substrate and/or microneedles, as well as other components, are formed from flexible materials, or have appropriate materials so as to be flexible, to allow the device to fit the contours of the biological barrier, such as the skin, vessel walls, or the eye, to which the device is applied. A flexible device facilitates more consistent penetration during use, since penetration can be limited by deviations in the attachment surface. For example, the surface of human skin is not flat due to dermatoglyphics (i.e. tiny wrinkles) and hair. Conformality of the flexible device to the skin can be further enhanced by using an external force, such as a uniform pressure, to aid insertion of the microneedles into the biological barrier.

c. Collection Chamber

The fluid collection chamber is selectably in connection with the microneedle bores or pores, such that a biological fluid can flow from the tissue surrounding the microneedle, through the microneedle, and into the collection chamber. Typically, the collection chamber is attached to, or integrated into, the substrate. The chamber should function to contain a biological fluid sample so as to permit analysis within the microneedle device or following transfer to a separate analytical device.

The collection chamber can be substantially rigid or readily deformable. The collection chamber can be formed from one or more polymers, metals, ceramics, semiconductor, or combinations thereof. In a preferred embodiment, the collection chamber contains a porous or absorbent material, such as a sponge, gel, or paper or polymeric strip. The material can be permanently contained or removable, and can function as a diagnostic element or substrate for use in analytical devices. The chamber can initially be empty or can contain a gas or one or more reagents in any form (e.g., liquid or solid particles). In one embodiment, at least a portion of the interior walls of the chamber are coated with a reagent for assaying the biological fluid.

In a preferred embodiment, the collection chamber is formed of an elastic material, such as an elastomeric polymer or rubber. For example, the collection chamber can be a collapsed balloon-like pouch that expands when the biological fluid is drawn into the collection chamber.

The collection chamber of a microneedle device can include a plurality of compartments that are temporarily or permanently isolated from one another and/or from a portion of the microneedles in an array. The device can, for example, be provided to collect or sense through different needles at different rates or at different times into the different compartments. Alternatively, some of the different compartments can contain analytical reagents which can be combined with the biological fluid sample, for example, by piercing, or otherwise removing, a barrier between the compartments, so as to allow the materials to mix for analysis.

Figure 4:
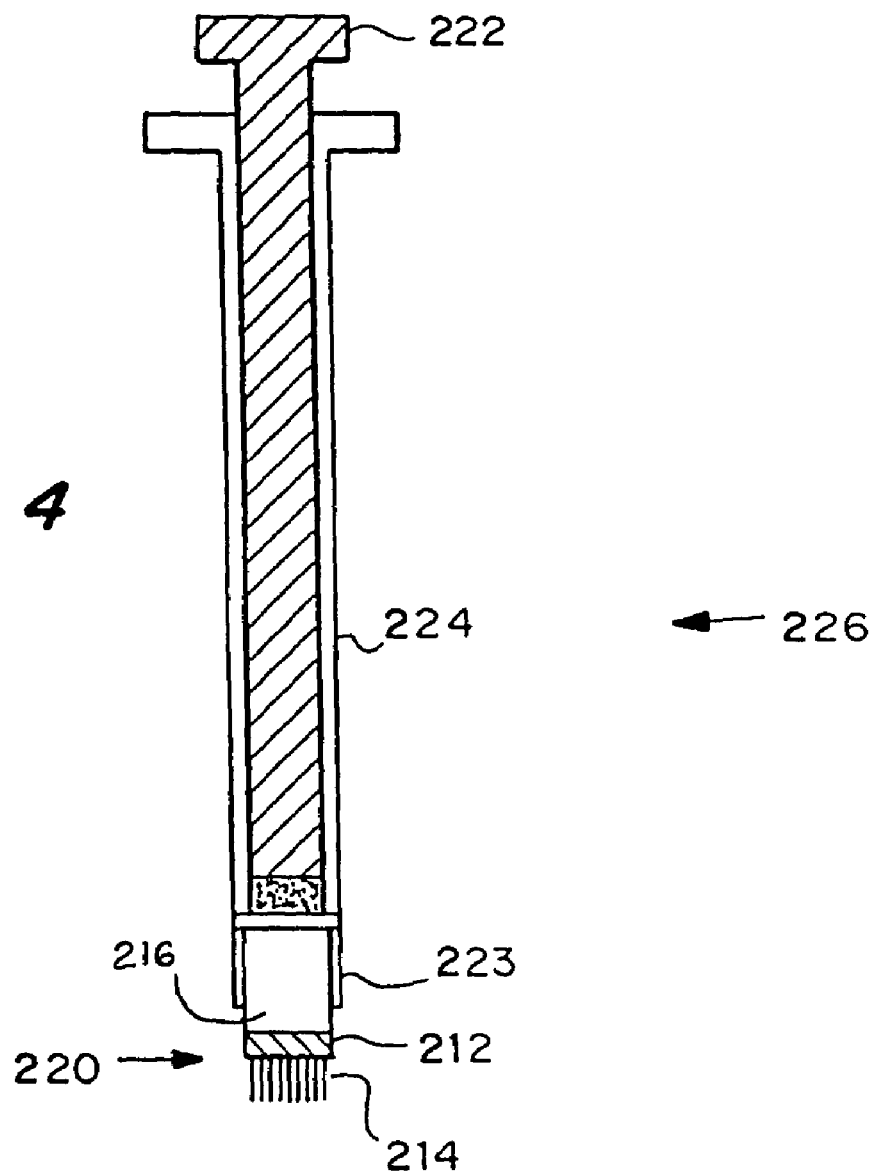
FIG. 4 is cross-sectional view of a preferred embodiment of a microneedle device connected to a standard-type syringe.

In a preferred embodiment, the collection chamber is a standard or Luer-Lock syringe adapted to be connected to a microneedle array. See FIG. 4 which illustrates a preferred embodiment wherein device 220 includes substrate 212 from which a three-dimensional array of microneedles 214 protrude. The device 220 also includes plunger 222 that is slidably secured to the upper surface of substrate 212 by plunger guide frame 224 using a restraint such as a Luer-lock interface 223. The substrate 212 can be attached or detached to a syringe 226 via a connector such as a Luer-lock type attachment 223. The plunger 222, guide frame (outer syringe housing) 224, and connector 223 connect to, form or contain reservoir 216. A Luer-lock type attachment alternatively may be used to secure the device to means, such as a pump, for controlling flow or transport through the device.

In another preferred embodiment, the collection chamber is adapted to receive and use standard glucose sensing strips, which can be loaded into the microneedle device before, during, or after the biological fluid is extracted.

Figure 2:
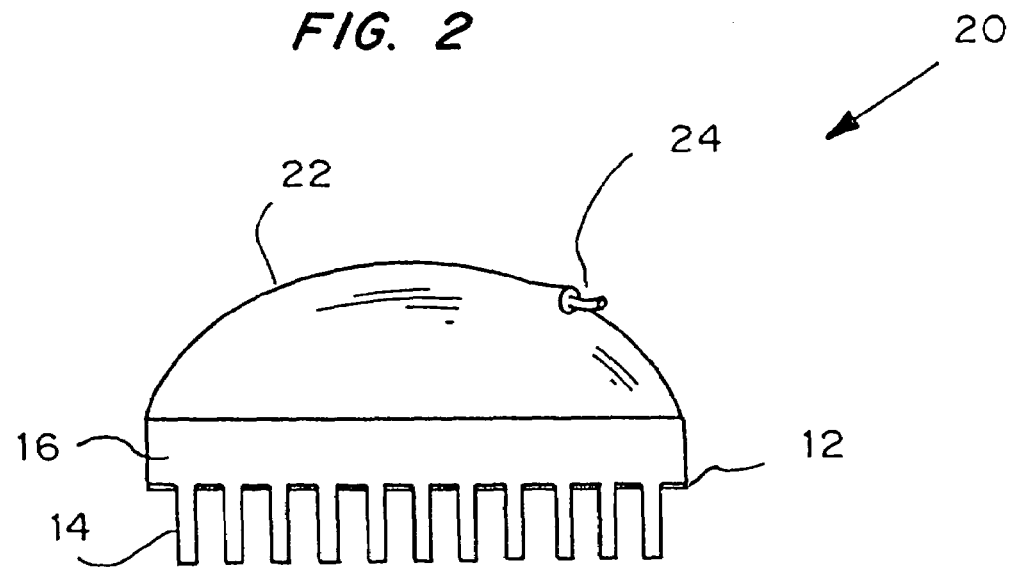
FIG. 2 is a cross-sectional view of another preferred embodiment of a microneedle device for fluid withdrawal.

Preferred embodiments of the microneedle device are shown in FIGS. 1-2. In FIG. 1, microneedle device 10 includes substrate 12 from which a three-dimensional array of microneedles 14 protrude. As shown, the annular bore of the microneedles 14 extends through the substrate 12. The device 10 also includes fluid collection chamber 16 which is in fluid connection with the microneedles 14. Fluid collection chamber 16 includes an access port 18 through which collected fluid can be withdrawn from collection chamber 16, and/or through which a withdrawing force, such as a vacuum, can be applied. In FIG. 2, microneedle device 20 includes substrate 12 from which a three-dimensional array of microneedles 14 protrude, and fluid collection chamber 16, as well as elastic cap 22 and one-way valve 24. The interior of elastic cap 22 is in communication with, or open to, fluid collection chamber 16.

d. Sensors

The sensing/analyzing function can occur in the microneedle or body of the device (e.g., in the fluid collection chamber), or external to the device following removal of a sample. The sensing device can be in or attached to one or more microneedles, integrated into the substrate, or within or in communication with the fluid collection chamber. Biosensors can be located on the microneedle surface, inside a hollow or porous microneedle, or inside a device in communication with the body tissue via the microneedle (solid, hollow, or porous).

In a preferred embodiment, the microneedle device provides a single-use collection means. In this design, the microneedle array is used to extract a single measurement and then is detached from a reusable base portion, if any, and disposed.

In one embodiment, the microneedle device is adapted to work with "laboratory-on-a-chip" devices, such as manufactured by Caliper Technologies, Palo Alto, Calif. (see, e.g., U.S. Pat. No. 5,852,495 to Parce and U.S. Pat. No. 5,876,675 to Kennedy); Aclara Biosciences, Hayward, Calif. (see, e.g., U.S. Pat. No. 5,858,188 to Soane et al. and U.S. Pat. No. 5,883,211 to Sassi et al.); and Nanogen, San Diego, Calif. (see, e.g., U.S. Pat. Nos. 5,605,662 and 5,632,957 to Heller et al.).

(i). Tapes of Sensors

Useful sensors may include sensors of pressure, temperature, chemicals, pH, and/or electro-magnetic fields. These microneedle biosensors can include four classes of principal transducers: potentiometric, amperometric, optical, and physiochemical. An amperometric sensor monitors currents generated when electrons are exchanged between a biological system and an electrode. Blood glucose sensors frequently are of this type.

Sensing information or signals can be transferred optically (e.g., refractive index) or electrically (e.g., measuring changes in electrical impedance, resistance, current, voltage, or combination thereof). For example, it may be useful to measure a change in the resistance of tissue to an electrical current, wherein different resistances are calibrated to signal that withdrawal has been completed.

In a preferred embodiment, the microneedle device may include an integrated sensor, such as a chemical sensor, biosensor, or other measurement system to form a complete extraction/measurement system. The unit can be constructed to function as a closed loop drug delivery unit, including drug delivery means, analyte recovery means, sensing means to measure the analyte, and control means to provide a signal to the drug delivery means. In a preferred embodiment, the unit would include subunits to withdraw fluid and calculate the concentration of glucose, for example, to determine the amount of insulin needed and deliver that amount of insulin.

The device can include means for assaying the amount of analyte extracted. For example, an assay method that results in a color change could be used. The change in color could be detected using a light beam that enters into a disposable collection chamber through a window on top. The analyte may also be detected in the chamber through the use of an enzyme electrode or biosensor. The analyte sensing system can include enzymes that react with the analyte of interest and either electrochemical or optical transducers that measure the content of reaction. Examples of such enzymes are glucose oxidase and glucose dehydrogenase.

An example of an enzyme electrode for glucose is a screen-printed electrode on the surface of which is immobilized glucose oxidase and an electron mediator such as ferrocene or its derivatives. Electrons generated by the oxidation of glucose are transferred from glucose oxidase to the electrode via the mediator. Thus, the concentration of glucose in the analyte solution is proportional to the current generated. Yet another detection mechanism may be used based on near-infrared spectroscopy. In this method, concentration of extracted glucose in a gel is detected by the absorption of the near-infrared light that passes through the chamber through two windows.

(ii). Microneedle as Sensing Element

In one embodiment, the microneedle is adapted to be the sensing element. For example, an assay material, such as glucose oxidase, can be (i) coated onto the external surface of hollow or solid microneedles, (ii) distributed within the pores of porous microneedles, or (iii) line or fill the bore(s) of hollow microneedles. See FIG. 3 which illustrates a cross sectional view of a preferred embodiment of a microneedle device 30 including microneedle 32, attached to substrate 34 and having hollow bore 36. In FIG. 3a, sensor material 38 is coated on the external surface of microneedle 32. In FIG. 3b, sensor material 38 is coated on the internal surface of hollow bore 36. In FIG. 3c, sensor material 38 is located within the pores of a porous microneedle 32. Solid microneedles can also hold or contain sensor material as in FIG. 3a, or as in FIG. 3c if the microneedles are porous. These various microneedle types and sensors can be used in different combinations within a device array.

In this embodiment, the assay material contacts the analyte for which it is selective and undergoes a change, such as an oxidation reaction. This change is communicated, either directly or indirectly, to the user. For example, change may be indicated optically (change in color or refractive index) or electrically. Alternatively, the change may induce a shift in pH that can be measured and communicated using conventional techniques. In more complex embodiments, the analyte may be adsorbed to the microneedle or a coating thereon, such that mechanical sensing can be used, for example, by measuring vibration changes caused by the adsorption.

(iii). Sensor Electronics

In a preferred embodiment, the sensors are selectively in communication with an electronics package. The electronics package typically includes a power source (e.g., a battery), as well as electronic hardware and software for the transduction, storage, transmission, and display of measured values. The electronics package can be selectively fixed to the microneedle device, for example, so that the electronics package can be reused with a new, disposable microneedle device. The electronics package can include a mechanism for wireless or wire-based transmission of measured values to a remote device for analysis and/or display. The electronics also may include mathematical manipulation of the sensed data, for example, to average measured values or eliminate outlying datapoints so as to provide more useful measurements.

The electronics package also can include software and hardware to initiate or automate the sensing and analysis processes. It may be desirable to design a microneedle device capable of taking multiple measurements to withdraw/sense samples on a preprogrammed schedule (e.g., periodic or random), for example, to monitor the blood plasma levels of an illegal drug. Such a device could be adapted for use with a transmitter designed to lock onto the wrist or ankle of a drug offender or other probationer. The device would then be able to randomly test the wearer without his knowledge in order to assess his compliance with orders to abstain from drug or alcohol use.

In an alternative embodiment, the electronics package includes a device for controlling the withdrawal or sensing process. For example, sensing could be activated based on elapsed time, body temperature, or in response to an external trigger (e.g., motion sensor or push-button). The electronics package, for example, could provide substantially instantaneous readings of glucose levels by depressing a button, or in a microneedle device (e.g., adapted to be worn for an extended period of time), the electronics could it could display a summary of intermittent glucose measurements taken automatically throughout the day. Such a microneedle device would be highly useful to diabetic patients to routinely monitor their blood glucose levels following insulin dosing, between or following meals, and at other times throughout the day.

(iv). Single Unit Multiple Sensing

A single microneedle device can be designed to provide multiple, preferably sequential, measurements. In a preferred embodiment, the device includes a plurality of discrete fluid collection chambers, each of which is in communication with a defined subset of microneedles in an array of microneedles. The sensing unit of the device can sense each of the collection chambers independently. The sensing can be triggered manually or device electronics can be preprogrammed to automatically trigger, for example at specific time intervals. The device can include a means for storing, displaying, or transmitting the multiple measured values as needed.

(v). Sensor Calibration

Calibration of the sensor can be accomplished using the concentration of a second analyte or the same analyte measured by another means. The primary analyte can be normalized, lowering extraction to extraction and site to site variability, by the concentration of the second analyte or same analyte from a separate measurement. Normalization may be a linear or non-linear relationship.

In a preferred embodiment for glucose sensing, a reusable sensor, which assays glucose concentration in interstitial fluid, can be calibrated daily by correlating interstitial fluid glucose values with values obtained from glucose measurements obtained from blood, similar to the approach used by Cygnus Inc.'s "Gluco-Watch."

e. Attachment Feature

In a preferred embodiment, the microneedle device includes an adhesive material to secure the microneedle device to the skin, temporarily immobilizing the microneedles while inserted into the skin to sense or withdraw fluid. The adhesive agent typically is applied to the substrate (in between the microneedles at their base) or to an attachment collar or tabs adjacent the microneedles.

Care must be taken so that any adhesive agent does not plug the bores of hollow microneedles. For example, the adhesive agent can be applied in a liquid solution by flooding the top of the substrate below the tips of the microneedles, such as from the side of an array of microneedles, or by using a three-dimensional printing process or spin coating. The solvent can then be evaporated from the adhesive agent solution, thereby precipitating or gelling the adhesive agent to yield a tacky surface. An alternate method of keeping the tips free of an applied adhesive agent is to choose materials of construction having a hydrophobicity or hydrophilicity to control the wetting of the surface to the microneedle tips.

Where a vacuum is used to induce fluid flow into the device, it may be necessary to provide means for creating a gas-tight seal around the edge of the device so that air is not drawn in through the microneedles at the biological barrier hole/microneedle shaft periphery. The attachment collar or adhesive material can be adapted to provide this function using techniques common to the those skilled in the art. One example is to design the attachment collar to function as a "suction-cup" and wet the interface of the skin and attachment collar with water or another physiologically acceptable sealant.

For sustained use, such as for taking sequential measurements, the device preferably is adapted to be worn by the user, by including a securing means for securing the whole device to the user's body. For example, the device can be integrated into an adhesive patch or an elastic band, which may be worn, for example, around the user's arm or ankle.

Feedback about Withdrawal

In a preferred embodiment, the microneedle device includes a feedback means so that the user can determine whether withdrawal and/or sensing has been completed. Representative feedback means include a sound, a color (change) indicator, or a change in the position or shape of a reservoir.

2. Manufacture of Microneedles

The microneedle devices are made by microfabrication processes, by creating small mechanical structures in silicon, metal, polymer, and other materials. These microfabrication processes are based on well-established methods used to make integrated circuits, electronic packages and other microelectronic devices, augmented by additional methods used in the field of micromachining. The microneedle devices can have dimensions as small as a few nanometers and can be mass-produced at low per-unit costs.

a. Microfabrication Processes

Microfabrication processes that may be used in making the microneedles disclosed herein include lithography; etching techniques, such as wet chemical, dry, and photoresist removal; thermal oxidation of silicon; electroplating and electroless plating; diffusion processes, such as boron, phosphorus, arsenic, and antimony diffusion; ion implantation; film deposition, such as evaporation (filament, electron beam, flash, and shadowing and step coverage), sputtering, chemical vapor deposition (CVD), epitaxy (vapor phase, liquid phase, and molecular beam), electroplating, screen printing, lamination, stereolithography, laser machining, and laser ablation (including projection ablation). See generally Jaeger, *Introduction to Microelectronic Fabrication* (Addison-Wesley Publishing Co., Reading Mass. 1988); Runyan, et al., *Semiconductor Integrated Circuit Processing Technology* (Addison-Wesley Publishing Co., Reading Mass. 1990); *Proceedings of the IEEE Micro Electro Mechanical Systems Conference* 1987-1998; Rai-Choudhury, ed., *Handbook of Microlithography, Micromachining & Microfabrication* (SPIE Optical Engineering Press, Bellingham, Wash. 1997); and Madou, *Fundamentals of Microfabrication* (CRC Press 1997).

The following methods are preferred for making microneedles.

(i). Electrochemical Etching of Silicon

In this method, electrochemical etching of solid silicon to porous silicon is used to create extremely fine (on the order of 0.01 µm) silicon networks which can be used as piercing structures. This method uses electrolytic anodization of silicon in aqueous hydrofluoric acid, potentially in combination with light, to etch channels into the silicon. By varying the doping concentration of the silicon wafer to be etched, the electrolytic potential during etching, the incident light intensity, and the electrolyte concentration, control over the ultimate pore structure can be achieved. The material not etched (i.e. the silicon remaining) forms the microneedles. This method has been used to produce irregular needle-type structures measuring tens of nanometers in width.

(ii). Plasma Etching

This process uses deep plasma etching of silicon to create microneedles with diameters on the order of 0.1 µm or larger. Needles are patterned directly using photolithography, rather than indirectly by controlling the voltage (as in electrochemical etching), thus providing greater control over the final microneedle geometry.

In this process, an appropriate masking material (e.g., metal) is deposited onto a silicon wafer substrate and patterned into dots having the diameter of the desired microneedles. The wafer is then subjected to a carefully controlled plasma based on fluorine/oxygen chemistries to etch very deep, high aspect ratio trenches into the silicon. See, e.g., Jansen, et al., "The Black Silicon Method IV: The Fabrication of Three-Dimensional Structures in Silicon with High Aspect Ratios for Scanning Probe Microscopy and Other Applications," *IEEE Proceedings of Micro Electro Mechanical Systems Conference*, pp. 88-93 (1995). Those regions protected by the metal mask remain and form the needles. This method is further described in Example 3 below.

(iii). Electroplating

In this process, a metal layer is first evaporated onto a planar substrate. A layer of photoresist is then deposited onto the metal to form a patterned mold which leaves an exposed-metal region in the shape of needles. By electroplating onto the exposed regions of the metal seed layer, the mold bounded by photoresist can be filled with electroplated material. Finally, the substrate and photoresist mold are removed, leaving the finished microneedle array. The microneedles produced by this process generally have diameters on the order of 1 µm or larger. See, e.g., Frazier, et al., "Two dimensional metallic microelectrode arrays for extracellular stimulation and recording of neurons", *IEEE Proceedings of the Micro Electro Mechanical Systems Conference*, pp. 195-200 (1993).

(iv). Other Processes

Another method for forming microneedles made of silicon or other materials is to use microfabrication techniques such as photolithography, plasma etching, or laser ablation to make a mold form (A), transferring that mold form to other materials using standard mold transfer techniques, such as embossing or injection molding (B), and reproducing the shape of the original mold form (A) using the newly-created mold (B) to yield the final microneedles (C). Alternatively, the creation of the mold form (A) could be skipped and the mold (B) could be microfabricated directly, which could then be used to create the final microneedles (C).

Another method of forming solid silicon microneedles is by using epitaxial growth on silicon substrates, as is utilized by Containerless Research, Inc. (Evanston, Ill., USA) for its products.

b. Hollow or Porous Microneedles

In a preferred embodiment, microneedles are made with pores or other pathways through which material may be transported. The following descriptions outline representative methods for fabricating either porous or hollow microneedles.

(i). Porous Microneedles

Rather than having a single, well-defined hole down the length of the needle, porous needles are filled with a network of channels or pores which allow conduction of fluid or energy through the needle shaft. It has been shown that by appropriate electrochemical oxidation of silicon, pore arrays with high aspect ratios and a range of different pore size regimes can be formed; these pore regimes are defined as (1) microporous regime with average pore dimensions less than 2 nm, (2) mesoporous regime with average pore sizes of between 2 nm and 50 nm, and (3) macroporous regime with pores greater than 50 mm. The mesoporous and macroporous regimes are expected to be most useful for drug delivery. Two approaches to porous needles are generally available, either (a) the silicon wafer is first made porous and then etched as described above to form needles or (b) solid microneedles are etched and then rendered porous, for example, by means of electrochemical oxidation, such as by anodization of a silicon substrate in a hydrofluoric acid electrolyte. The size distribution of the etched porous structure is highly dependent on several variables, including doping kind and illumination conditions, as detailed in Lehmann, "Porous Silicon—A New Material for MEMS", *IEEE Proceedings of the Micro Electro Mechanical Systems Conference*, pp. 1-6 (1996). Porous polymer or metallic microneedles can be formed, for example, by micromolding a polymer containing a volatilizable or leachable material, such as a volatile salt, dispersed in the polymer or metal, and then volatilizing or leaching the dispersed material, leaving a porous polymer matrix in the shape of the microneedle.

(ii). Hollow Needles

Three-dimensional arrays of hollow microneedles can be fabricated, for example, using combinations of dry etching processes (Laermer, et al., "Bosch Deep Silicon Etching: Improving Uniformity and Etch Rate for Advanced MEMS Applications," *Micro Electro Mechanical Systems*, Orlando, Fla., USA, (Jan. 17-21, 1999); Despont et al., "High-Aspect-Ratio, Ultrathick, Negative-Tone Near-UV Photoresist for MEMS", *Proc. of IEEE* 10th *Annual International Workshop on MEMS*, Nagoya, Japan, pp. 518-522 (Jan. 26-30, 1997)); micromold creation in lithographically-defined and/or laser ablated polymers and selective sidewall electroplating; or direct micromolding techniques using epoxy mold transfers.

One or more distinct and continuous pathways are created through the interior of microneedles. In a preferred embodiment, the microneedle has a single annular pathway along the center axis of the microneedle. This pathway can be achieved by initially chemically or physically etching the holes in the material and then etching away microneedles around the hole. Alternatively, the microneedles and their holes can be made simultaneously or holes can be etched into existing microneedles. As another option, a microneedle form or mold can be made, then coated, and then etched away, leaving only the outer coating to form a hollow microneedle. Coatings can be formed either by deposition of a film or by oxidation of the silicon microneedles to a specific thickness, followed by removal of the interior silicon. Also, holes from the backside of the wafer to the underside of the hollow needles can be created using a front-to-backside infrared alignment followed by etching from the backside of the wafer.

a. Silicon Microneedles

Figure 5A:
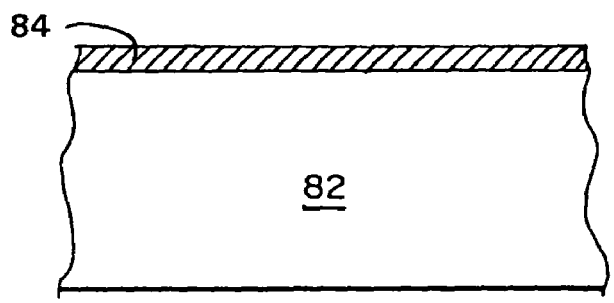
FIGS. 5a-e are side cross-sectional views of a method for making microneedles.
Figure 5B:
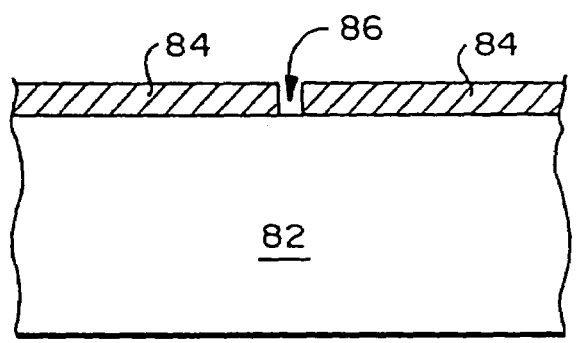
Figure 5C:
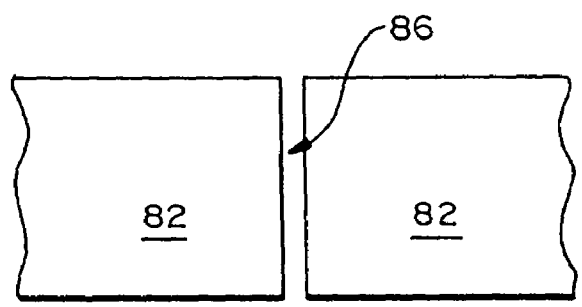
Figure 5D:
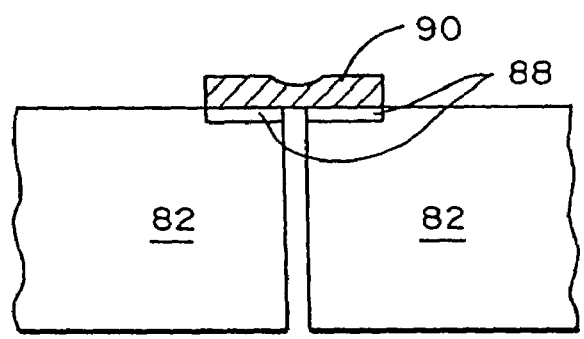
Figure 5E:
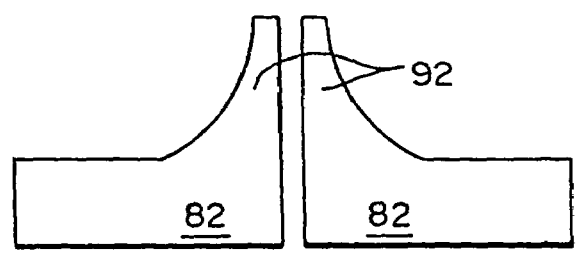

One method for hollow needle fabrication is to replace the solid mask used in the formation of solid needles by a mask that includes a solid shape with one or more interior regions of the solid shape removed. One example is a "donut-shaped" mask. Using this type of mask, interior regions of the needle are etched simultaneously with their side walls. Due to lateral etching of the inner side walls of the needle, this may not produce sufficiently sharp walls. In that case, two plasma etches may be used, one to form the outer walls of the microneedle (i.e., the 'standard' etch), and one to form the inner hollow core (which is an extremely anisotropic etch, such as in inductively-coupled-plasma "ICP" etch). For example, the ICP etch can be used to form the interior region of the needle followed by a second photolithography step and a standard etch to form the outer walls of the microneedle. FIG. 5*a* represents a silicon wafer 82 with a patterned photoresist layer 84 on top of the wafer 82. The wafer 82 is anisotropically etched (FIG. 5*b*) to form a cavity 86 through its entire thickness (FIG. 5*c*). The wafer 82 is then coated with a chromium layer 88 followed by a second photoresist layer 90 patterned so as to cover the cavity 86 and form a circular mask for subsequent etching (FIG. 5*d*). The wafer 82 is then etched by a standard etch to form the outer tapered walls 92 of the microneedle (FIG. 5*e*).

Figure 6A:
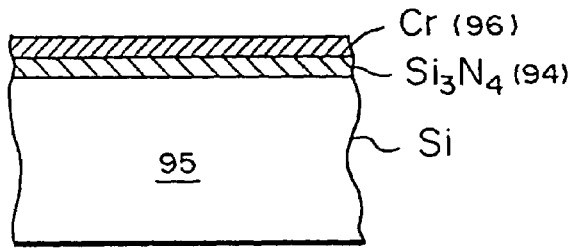
FIGS. 6a-g are side cross-sectional views of a method for making a hollow microneedle.
Figure 6B:
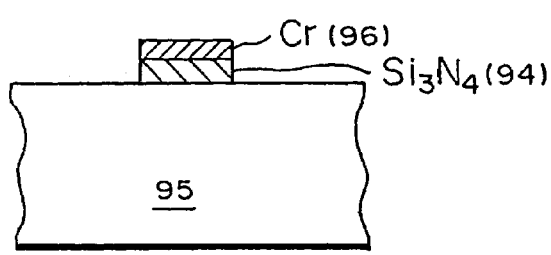
Figure 6E:
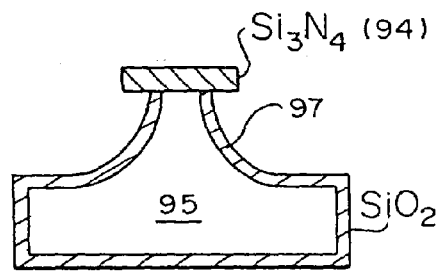
Figure 6C:
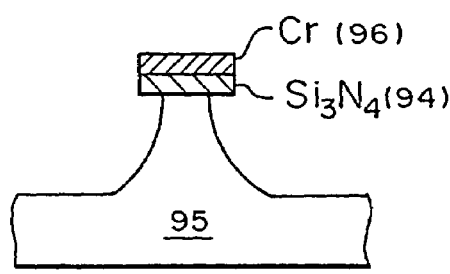
Figure 6F:
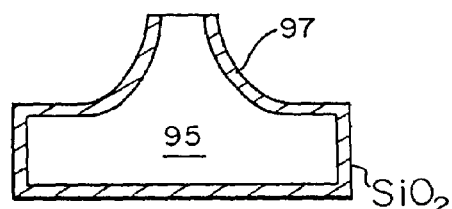
Figure 6D:
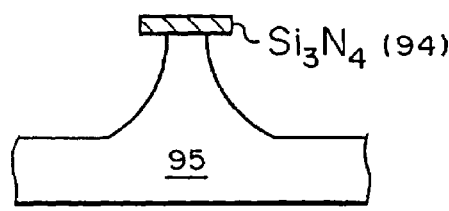
Figure 6G:
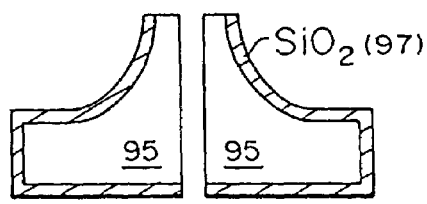

Alternatively, this structure can be achieved by substituting the chromium mask used for the solid microneedles described in Example 3 by a silicon nitride layer 94 on the silicon substrate 95 covered with chromium 96, deposited as shown in FIG. 6*a* and patterned as shown in FIG. 6*b*. Solid microneedles are then etched as described in Example 3 as shown FIG. 6*c*, the chromium 96 is stripped (FIG. 6*d*), and the silicon 95 is oxidized to form a thin layer of silicon dioxide 97 on all exposed silicon surfaces (FIG. 6*e*). The silicon nitride layer 94 prevents oxidation at the needle tip. The silicon nitride 94 is then stripped (FIG. 6*f*), leaving exposed silicon at the tip of the needle and oxide-covered silicon 97 everywhere else. The needle is then exposed to an ICP plasma which selectively etches the inner sidewalls of the silicon 95 in a highly anisotropic manner to form the interior hole of the needle (FIG. 6*g*).

Another method uses the solid silicon needles described previously as 'forms' around which the actual needle structures are deposited. After deposition, the forms are etched away, yielding the hollow structures. Silica needles or metal needles can be formed using different methods. Silica needles can be formed by creating needle structures similar to the ICP needles described above prior to the oxidation described above. The wafers are then oxidized to a controlled thickness, forming a layer on the shaft of the needle form which will eventually become the hollow microneedle. The silicon nitride is then stripped and the silicon core selectively etched away (e.g., in a wet alkaline solution) to form a hollow silica microneedle.

In a preferred embodiment, an array of hollow silicon microtubes is made using deep reactive ion etching combined with a modified black silicon process in a conventional reactive ion etcher, as described in Example 4 below. First, arrays of circular holes are patterned through photoresist into $SiO_2$, such as on a silicon wafer. Then the silicon can be etched using deep reactive ion etching (DRIE) in an inductively coupled plasma (ICP) reactor to etch deep vertical holes. The photoresist is then removed. Next, a second photolithography step patterns the remaining $SiO_2$ layer into circles concentric to the holes, leaving ring shaped oxide masks surrounding the holes. The photoresist is then removed and the silicon wafer again deep silicon etched, such that the holes are etched completely through the wafer (inside the $SiO_2$ ring) and simultaneously the silicon is etched around the $SiO_2$ ring leaving a cylinder.

This latter process can be varied to produce hollow, tapered microneedles. After an array of holes is fabricated as described above, the photoresist and $SiO_2$ layers are replaced with conformal DC sputtered chromium rings. The second ICP etch is replaced with a $SF_6/O_2$ plasma etch in a reactive ion etcher (RIE), which results in positively sloping outer sidewalls. Henry, et al., "Micromachined Needles for the Transdermal Delivery of Drugs," *Micro Electro Mechanical Systems*, Heidelberg, Germany, pp. 494-98 (Jan. 26-29, 1998).

b. Metal Microneedles

Metal needles can be formed by physical vapor deposition of appropriate metal layers on solid needle forms, which can be made of silicon using the techniques described above, or which can be formed using other standard mold techniques such as embossing or injection molding. The metals are selectively removed from the tips of the needles using electropolishing techniques, in which an applied anodic potential in an electrolytic solution will cause dissolution of metals more rapidly at sharp points, due to concentration of electric field lines at the sharp points. Once the underlying silicon needle forms have been exposed at the tips, the silicon is selectively etched away to form hollow metallic needle structures. This process could also be used to make hollow needles made from other materials by depositing a material other than metal on the needle forms and following the procedure described above.

A preferred method of fabricating hollow metal microneedles utilizes micromold plating techniques, which are described as follows and in Examples 5 and 6. In a method for making metal microtubes, which does not require dry silicon etching, a photo-defined mold first is first produced, for example, by spin casting a thick layer, typically 150 µm, of an epoxy (e.g., SU-8) onto a substrate that has been coated with a thin sacrificial layer, typically about 10 to 50 nm. Arrays of cylindrical holes are then photolithographically defined through the epoxy layer, which typically is about 150 µm thick. (Despont, et al., "High-Aspect-Ratio, Ultrathick, Negative-Tone Near-UV Photoresist for MEMS," *Proc. of IEEE 10th Annual International Workshop on MEMS*, Nagoya, Japan, pp. 518-22 (Jan. 26-30, 1997)). The diameter of these cylindrical holes defines the outer diameter of the tubes. The upper surface of the substrate, the sacrificial layer, is then partially removed at the bottom of the cylindrical holes in the photoresist. The exact method chosen depends on the choice of substrate. For example, the process has been successfully performed on silicon and glass substrates (in which the upper surface is etched using isotropic wet or dry etching techniques) and copper-clad printed wiring board substrates. In the latter case, the copper laminate is selectively removed using wet etching. Then a seed layer, such as Ti/Cu/Ti (e.g., 30 nm/200 nm/30 nm), is conformally DC sputter-deposited onto the upper surface of the epoxy mold and onto the sidewalls of the cylindrical holes. The seed layer should be electrically isolated from the substrate. Subsequently, one or more electroplatable metals or alloys, such as Pd, Pt, Ni, NiFe, Au, Cu, or Ti, are electroplated onto the seed layer. The surrounding epoxy is then removed, leaving microtubes which each have an interior annular hole that extends through the base metal supporting the tubes. The rate and duration of electroplating is controlled in order to define the wall thickness and inner diameter of the microtubes. In one embodiment, this method was used to produce microtubes having a height of between about 150 and 250 µm, an outer diameter of between about 40 and 120 µm, and an inner diameter of between about 30 and 110 µm (i.e., having a wall thickness of 10 µm). In a typical array, the microtubes have a tube center-to-center spacing of about 150 µm, but can vary depending on the desired needle density.

A variation of this method is preferred for forming tapered microneedles. As described above, photolithography yields holes in the epoxy which have vertical sidewalls, such that the resulting shafts of the microneedles are straight, not tapered. This vertical sidewall limitation can be overcome by molding a preexisting 3D structure, i.e., a mold-insert. The subsequent removal of the mold-insert leaves a mold which can be surface plated similarly to the holes produced by photolithography described above.

Alternatively, non-vertical sidewalls can be produced directly in the polymeric mold into which electroplating will take place. For example, conventional photoresists known in the art can be exposed and developed in such as way as to have the surface immediately adjacent to the mask be wider than the other surface. Specialized greyscale photoresists in combination with greyscale masks can accomplish the same effect. Laser-ablated molds can also be made with tapered sidewalls, e.g., by optical adjustment of the beam (in the case of serial hole fabrication) or of the reticle or mold during ablation (in the case of projection ablation).

To form hollow tapered microneedles, the mold-insert is an array of solid silicon microneedles, formed as described in Henry, et al., "Micromachined Needles for the Transdermal Delivery of Drugs," *Micro Electro Mechanical Systems*, Heidelberg, Germany, Jan. 26-29, pp. 494-98 (1998). First, a layer of a material, such as an epoxy (e.g., SU-8) or a polydimethylsiloxane ("PDMS"), is spin cast onto the array of silicon microneedles to completely blanket the entire array. The epoxy settles during pre-bake to create a planar surface above the silicon needle tips; the material is then fully pre-baked, photolithographically cross-linked, and post-baked.

The upper surface of the epoxy is then etched away, for example with an $O_2/CHF_3$ plasma, until the needle tips are exposed, preferably leaving between about 1 and 5 µm of tip protruding from the epoxy. The silicon is then selectively removed, for example by using a $SF_6$ plasma or a $HNO_3/HF$ solution. The remaining epoxy micromold is the negative of the microneedles and has a small diameter hole where the tip of the microneedle formerly protruded.

After the removal of the silicon, a seed layer, such as Ti—Cu—Ti, is conformally sputter-deposited onto the epoxy micromold. Following the same process sequence described for hollow metal microtubes, one or more electroplatable metals or alloys (such as Ni, NiFe, Au, Pd, Pt, or Cu) are electroplated onto the seed layer. Finally, the epoxy is removed, for example by using an $O_2/CHF_3$ plasma, leaving an array of hollow metal microneedles. An advantage of using PDMS in this application is that the micromold can be physically removed from the silicon mold insert by mechanical means, such as peeling, without damaging the silicon mold insert, thus allowing the silicon mold insert to be reused. Furthermore, the electroplated microneedles can be removed from the PDMS mold by mechanical means, for example by peeling, thereby allowing the PDMS to also be reused.

In a preferred embodiment, this method is used to produce microneedles having a height of between about 150 and 350 µm, an outer diameter of between about 40 and 120 µm, and an inner diameter of between about 20 and 100 µm. In a typical array, the microneedles have a center-to-center spacing of between about 150 and 300 µm, but can vary depending on the desired needle density. Tapered microneedles preferably are 200 to 300 µm in height with a base diameter of 80 µm, a tip diameter of 30 µm, and a needle-to-needle spacing of 150 µm.

c. Silicon Dioxide Microneedles

Hollow microneedles formed of silicon dioxide can be made by oxidizing the surface of the silicon microneedle forms (as described above), rather than depositing a metal and then etching away the solid needle forms to leave the hollow silicon dioxide structures. This method is illustrated in FIGS. 7a-d. FIG. 7a shows an array 124 of needle forms 126 with masks 128 on their tips. In FIG. 7b, the needle forms 126 have been coated with a layer 130 of metal, silicon dioxide or other material. FIG. 7c shows the coated needle forms 126 with the masks 128 removed. Finally, in FIG. 7d, the needle forms 126 have been etched away, leaving hollow needles 130 made of metal, silicon dioxide, or other materials.

In one embodiment, hollow, porous, or solid microneedles are provided with longitudinal grooves or other modifications to the exterior surface of the microneedles. Grooves, for example, should be useful in directing the flow of molecules along the outside of microneedles.

d. Polymer Microneedles

In a preferred method, polymeric microneedles are made using microfabricated molds. For example, the molds can be made as described herein and injection molding techniques can be applied to form the microneedles in the molds (Weber, et al., "Micromolding—a powerful tool for the large scale production of precise microstructures", Proc. *SPIE—International Soc. Optical Engineer.* 2879: 156-67 (1996); Schift, et al., "Fabrication of replicated high precision insert elements for micro-optical bench arrangements" *Proc. SPIE—International Soc. Optical Engineer.* 3513: 122-34 (1998)). Suitable molds can be formed, for example, from epoxy, silicon, or metal, using or adapting known microfabrication techniques. These micromolding techniques are preferred, as they can provide relatively less expensive replication, i.e. lower cost of mass production. In a preferred embodiment, the polymer is biodegradable.

3. Biological Fluids for Withdrawal or Sensing

The devices disclosed herein are useful in the transport of biological fluids from within or across a variety of biological barriers including the skin (or parts thereof); the blood-brain barrier; mucosal tissue; blood vessels; lymphatic vessels; cell membranes; epithelial tissue; and endothelial tissue. The biological barriers can be in humans or other types of animals, as well as in plants, insects, or other organisms, including bacteria, yeast, fungi, and embryos. In preferred embodiments, biological fluids are withdrawn from skin, more preferably human skin, for minimally invasive diagnostic sensing.

Biological fluids useful with the devices described herein include blood, lymph, interstitial fluid, and intracellular fluid. In a preferred embodiment, the biological fluid to be withdrawn or sensed is interstitial fluid.

A variety of analytes are routinely measured in the blood, lymph or other body fluids. Examples of typical analytes that can be measured include blood sugar (glucose), cholesterol, bilirubin, creatine, various metabolic enzymes, hemoglobin, heparin, hematocrit, vitamin K or other clotting factors, uric acid, carcinoembryonic antigen or other tumor antigens, and various reproductive hormones such as those associated with ovulation or pregnancy. Other substances or properties that would be desirable to detect include lactate (important for athletes), oxygen, pH, alcohol, tobacco metabolites, and illegal drugs (important for both medical diagnosis and law enforcement).

In a preferred embodiment, interstitial fluids are removed from the dermis or epidermis across the stratum corneum to assay for glucose concentration, which is useful in aiding diabetics in determining their required insulin dose.

4. Using the Microneedle Device

The device is applied to the skin or other biological barrier at the site where the sample is to be collected or measured. Then, biological fluid, or a component thereof, is drawn into or through the pores or bores of the microneedles, and optionally collected in the collection chamber. Alternatively, where the microneedles function as the sensor, sensing occurs without transfer of biological fluid into a collection chamber.

a. Feedback about Penetration of the Microneedles into the Tissue

The user of the microneedle device typically can determine if the microneedles have been properly inserted into the skin or other tissue through visual or tactile means, that is assessing whether the substrate has been pressed essentially flush to the tissue surface. A coloring agent can be used to enhance the visual feedback by indicating a color change triggered by biological fluid filing the collection chamber.

In a more complex embodiment, an electrical or chemical measurement is adapted to provide the feedback. For example, penetration can be determined by measuring a change in electrical resistance at the skin or other tissue, or a pH change. Alternately, needle-to-needle electrical resistance can be measured. In a preferred embodiment, the microneedle device includes a disposable cartridge containing the microneedles. In these devices, an LED (e.g., green light/red light) or liquid crystal display can be provided with the reusable portion or the device.

b. Initiating and Controlling Fluid Withdrawal

In a preferred embodiment, the microneedle device is capable of transporting molecules across or from the tissue at a useful rate. That rate will, of course, depend on the particular application. For assaying blood glucose, for example, the device preferably withdraws at least between about 5 and 10 µl of interstitial fluid, preferably in about a minute or less time. For other applications, it may be desirable to apply the device to the barrier for several hours or more in order to monitor the changing blood plasma level of a particular analyte, such as an exogenous drug or hormone level, for example on a real-time basis or to obtain a time-averaged value.

The rate of withdrawal can be controlled by altering one or more of several design variables. For example, the amount of material flowing through the needles can be controlled by manipulating the volumetric through-capacity of a single device array, for example, by using more or fewer microneedles, by increasing or decreasing the number or diameter of the bores in the microneedles, by filling at least some of the microneedle bores with a diffusion-limiting material, or by varying the driving force applied to the biological fluid. It is preferred, however, to simplify the manufacturing process by limiting the needle design to two or three "sizes" of microneedle arrays to accommodate, for example small, medium, and large volumetric flows, for which the withdrawal rate is controlled by other means.

The flow of biological fluid from the tissue through the microneedle and into the collection chamber or into contact with the sensors occurs due to capillary action, diffusion, or is induced using conventional mechanical pumps or nonmechanical driving forces, such as electroosmosis or electrophoresis, thermal gradients, or convection. For example, in electroosmosis, electrodes are positioned on the biological barrier surface, on one or more microneedles, and/or on the substrate adjacent the needles, to create a convective flow which carries charged ionic species and/or neutral molecules toward and/or through at least one of the microneedles.

Transportation of molecules through the microneedles can be controlled or monitored using, for example, various combinations of semi-permeable membranes, valves, pumps, sensors, actuators, and microprocessors. These components can be produced using standard manufacturing or microfabrication techniques. Actuators that may be useful with the microneedle devices disclosed herein include micropumps, microvalves, and positioners.

In a preferred embodiment, the microneedle device is used in combination with another mechanism that enhances the permeability of the biological barrier, for example by increasing cell membrane disruption, using electric fields, ultrasound, chemical enhancers, vacuum, viruses, pH, heat, and/or light. Chemical and/or physical enhancers can be applied to the biological barrier at the site of insertion of the device before or during the withdrawal of the device, for example, to draw analyte closer to the skin surface.

(i). Bulk Flow Extraction

A preferred microneedle device is shown in FIG. 2 and described above. Microneedle device 20 preferably is operated as follows. After or simultaneously with the insertion of device 20 into, for example, the skin, manual pressure is applied to elastic cap 22 so as to deform (compress) it and reduce the interior volume of elastic cap 22 and fluid collection chamber 16. The deformation causes gas within the cap and chamber to be purged from the device via one-way valve 24. As elastic cap 22 returns to its undeformed (uncompressed) shape, pressure is reduced within the interior volume, creating a pressure differential or vacuum, which causes the interstitial fluid, to be drawn through the microneedles 14 and into fluid collection chamber 16, until the pressure is equalized. Once in the collection chamber 16, the fluid sample can be analyzed by withdrawing device 20 from the skin, again depressing elastic cap 22, to force the sample out of the chamber either through the microneedles 14 or one-way valve 24, and, for example, onto a diagnostic strip or into a container adapted for the particular analytical method to be employed.

Other spring means can be adapted to cause a change in the volume, and thus internal pressure, of the collection chamber. For example, the fluid collection chamber can be adapted to have a movable, rigid top with fixed, rigid side walls, wherein the interface between the walls and top form a gas-tight seal (such as by using a gasket). The volume of the piston-like apparatus can be expanding by activating one or more compressed springs to move the top of the chamber as desired, thereby reducing the pressure in the collection chamber.

In an alternative embodiment, withdrawal can be initiated by activating an osmotic pump, as described, for example, in U.S. Pat. No. 4,320,758 to Eckenhoff, which has been engineered to create a volume expansion/pressure reduction in the collection chamber to draw biological fluid to be drawn into the collection chamber.

In a preferred embodiment, withdrawal is conducted using a microneedle device fitted to a Luer-Lock syringe or similar conventionally-used devices that currently uses hypodermic needles in the barrier penetration method.

(ii). Diffusion-Based Extraction

One preferred embodiment uses diffusion to move the analyte fluid into the fluid collection chamber. A microneedle device using this method generally includes microneedle bores or pores, and/or a fluid collection chamber, that are filled with a diffusion medium, such as water, a saline solution, or a gel, which is physiologically compatible with the biological barrier tissue. Once the needle is inserted into the biological barrier (e.g., the skin), the diffusion medium contacts the biological fluid. Typically, the diffusion medium in the microneedles initially contains none of the analyte to be measured; therefore, analyte at a higher concentration in the biological fluid diffuses into the diffusion medium in the microneedle until a detectable level of analyte in collected or measured. This should be achieved rapidly due to the very small size/length of the microneedles, thereby providing an analyte concentration for sensing that is rapidly response to that in the tissue.

(iii). Hybrid Bulk Flow/Diffusion

In another embodiment, the microneedle device is designed to employ a combination of forces to drive the analyte into the collection chamber. A preferred hybrid design includes the preferred bulk flow microneedle device described above, but with two primary differences. First, the fluid collection chamber has no one-way valve and contains a fluid diffusion medium, preferably physiological saline. Second, a temporary barrier is interposed between the fluid collection chamber and the base of the microneedles. The temporary barrier can be a fracturable membrane, mechanical gate, or other means for containing the diffusion medium within the device until the barrier is broken or removed at a selected time to permit flow of molecules between the microneedles and fluid collection chamber.

In a preferred embodiment, the temporary barrier is an easily fracturable membrane. The device can function as follows: The microneedles first are inserted into the skin of the user. Then the user depresses the elastic cap, causing the fluid diffusion medium to fracture the membrane and fill the bores or pores of the microneedles and contact the biological fluid. After the user releases the elastic cap, it partially or fully returns to its undeformed shape, reducing the pressure in the interior and causing a mixture of the biological fluid and diffusion medium to be drawn through the microneedles and into fluid collection chamber. Once bulk fluid flow ceases, diffusion may continue until the concentration of biological fluid or analyte equilibrates. The mixture can be assayed as described herein, considering the dilution effect induced by the presence of the diffusion medium.

Any of these embodiments of the microneedle device can be adapted to function a series of micro-assays (e.g., as can be provided with an electronics package) or single assays (e.g., standard glucose strips).

e. Multi-Cartridge Microneedle Device

A modification of the disposable, single use microneedle device utilizes a reusable portion providing the withdrawal force (e.g., suction) or electronics package in combination with a cartridge containing one or more, preferably a plurality, of single-use, disposable microneedle devices for collection and/or sensing. For example, the cartridge can be a circular disk having 10 or 12 microneedle arrays connected to a single-assay element, wherein the cartridge can be loaded into and unloaded from the reusable portion. The triggering device can, for example, be designed to move a new microneedle array into position, withdraw or sense the sample of biological fluid, and then eject or immobilize the used microneedle array. This type of reusable triggering device also can include a power source, such as a battery, used to operate a built-in measurement device, for example, for analyte measurement of interstitial fluids.

In one embodiment, the devices are provided in a multi-pack (e.g., six or twelve pack) form of complete devices, that is, each device is fully sufficient for use. Individual devices can be separated as needed for each sensing measurement.

The present invention will be further understood with reference to the following non-limiting examples.

EXAMPLE 1

Transport of Molecules Through Microneedles Inserted into Skin

Studies were performed to demonstrate transport of molecules using either solid silicon microneedles or using hollow silicon microneedles. Transport was measured across human cadaver epidermis in vitro using Franz diffusion chambers at 37° C. using methods described in Henry, et al., "Microfabricated microneedles: A novel method to increase transdermal drug delivery" *J. Pharm. Sci.* 87:922-25 (1998).

Removal of calcein was measured. Removal refers to the ability to transport calcein from the viable epidermis side of the epidermis to the stratum corneum side. This is the direction of transport associated with removing from the body compounds found in the body, such as glucose. Other compounds were tested for delivery only.

In all cases shown in Table 1, transport of these compounds across skin occurred at levels below our detection limit when no needles were inserted into the skin. When solid microneedles were inserted into the skin and left in place, large skin permeabilities were measured, indicating that the microneedles had created pathways for transport across the skin. Furthermore, in all cases, when solid microneedles were inserted into the skin and then removed, even greater skin permeabilities resulted. Finally, when hollow microneedles were inserted into the skin and left in place, still greater skin permeabilities resulted for those compounds tested. These studies show that microneedles can dramatically increase skin permeability and can thereby increase transport of a number of different compounds across the skin. It also shows that when solid microneedles are used, a preferred embodiment involves inserting and then removing microneedles, rather than leaving them in place. It also shows that using hollow microneedles are a preferred embodiment over the use of solid microneedles.

TABLE 1

Effect of Microneedles on Permeability of Skin to Drugs (cm/hr)

| Compound | No needles | Solid needles inserted | Solid needles inserted and removed | Hollow needles inserted |
|---|---|---|---|---|
| Calcein delivery | ** | $4 \times 10^{-3}$ | $1 \times 10^{-2}$ | $1 \times 10^{-1}$ |
| Calcein removal | ** | $2 \times 10^{-3}$ | $1 \times 10^{-2}$ | n.a. |
| Insulin delivery | ** | $1 \times 10^{-4}$ | $1 \times 10^{-2}$ | n.a. |
| Bovine serum albumin delivery | ** | $9 \times 10^{-4}$ | $8 \times 10^{-3}$ | $9 \times 10^{-2}$ |

** means that the transport was below the detection limit.
n.a. means that the data are not available.

EXAMPLE 2

Flow of Water Through Hollow Microneedles

To demonstrate that fluid can be forced through hollow microneedles at meaningful rates, the flow rate of water through a microneedle array was measures as a function of pressure. The array used contained 100 hollow silicon microneedles having an inner diameter of 50 μm and an outer diameter of 80 μm. The results, which are shown in Table 2, demonstrate that significant flow rates of water through microneedles can be achieved at modest pressures. The measured flow rates are comparable to flow rates through hypodermic needles attached to syringes.

TABLE 2

Flow Rate of Water Through Hollow Silicon Microneedles As a Function of Applied Pressure

| Pressure (psi) | Flow rate (ml/min) |
|---|---|
| 1.0 | 16 |
| 1.5 | 24 |
| 2.0 | 31 |
| 2.5 | 38 |
| 3.0 | 45 |

EXAMPLE 3

Fabrication of Solid Silicon Microneedles

A chromium masking material was deposited onto silicon wafers and patterned into dots having a diameter approximately equal to the base of the desired microneedles. The wafers were then loaded into a reactive ion etcher and subjected to a carefully controlled plasma based on fluorine/oxygen chemistries to etch very deep, high aspect ratio valleys into the silicon. Those regions protected by the metal mask remain and form the microneedles.

<100>-oriented, prime grade, 450-550 μm thick, 10-15 Ω-cm silicon wafers (Nova Electronic Materials Inc., Richardson, Tex.) were used as the starting material. The wafers were cleaned in a solution of 5 parts by volume deionized water, 1 part 30% hydrogen peroxide, and 1 part 30% ammonium hydroxide (J. T. Baker, Phillipsburg, N.J.) at approximately 80° C. for 15 minutes, and then dried in an oven (Blue M Electric, Watertown, Wis.) at 150° C. for 10 minutes. Approximately 1000 Å of chromium (Mat-Vac Technology, Flagler Beach, Fla.) was deposited onto the wafers using a DC-sputterer (601 Sputtering System, CVC Products, Rochester, N.Y.). The chromium layer was patterned into 20 by 20 arrays of 80 μm diameter dots with 150 μm center-to-center spacing using the lithographic process described below.

A layer of photosensitive material (1827 photoresist, Shipley, Marlborough, Mass.) was deposited onto the chromium layer covering the silicon wafers. A standard lithographic mask (Telic, Santa Monica, Calif.) bearing the appropriate dot array pattern was positioned on top of the photoresist layer. The wafer and photoresist were then exposed to ultraviolet (UV) light through the mask by means of an optical mask aligner (Hybralign Series 500, Optical Associates, Inc., Milpitas, Calif.). The exposed photoresist was removed by soaking the wafers in a liquid developer (354 developer, Shipley, Marlborough, Mass.) leaving the desired dot array of photoresist on the chromium layer. Subsequently, the wafers were dipped into a chromium etchant (CR-75; Cyanteck Fremont, Calif.), which etched the chromium that had been exposed during the photolithography step, leaving dot arrays of chromium (covered with photoresist) on the surface of the silicon wafer. The photoresist still present on the chromium dots formed the masks needed for fabrication of the microneedles, described below.

The microneedles were fabricated using a reactive ion etching techniques based on the Black Silicon Method developed at the University of Twente. The patterned wafers were etched in a reactive ion etcher (700 series wafer/batch Plasma Processing System, Plasma Therm, St. Petersburg, Fla.) with means for ensuring good thermal contact between the wafers and the underlying platen (Apiezon N, K. J. Lesker, Clairton, Pa.). The wafers were etched using the following gases and conditions: $SF_6$ (20 standard cubic centimeters per minute) and $O_2$ (15 standard cubic centimeters per minute) at a pressure of 150 mTorr and a power of 150 W for a run time of approximately 250 minutes. These conditions caused both deep vertical etching and slight lateral underetching. By controlling the ratio of flow rates of the $SF_6$ and $O_2$ gases used to form the plasma, the aspect ratio of the microneedles could be adjusted. The regions protected by the chromium masks remained and formed the microneedles. Etching was allowed to proceed until the masks fell off due to underetching, resulting in an array of sharp silicon spikes.

EXAMPLE 4

Fabrication of Silicon Microtubes

Three-dimensional arrays of microtubes were fabricated from silicon, using deep reactive ion etching combined with a modified black silicon process in a conventional reactive ion etcher. The fabrication process is illustrated in FIGS. 8a-d. First, arrays of 40 μm diameter circular holes 132 were patterned through photoresist 134 into a 1 μm thick $SiO_2$ layer 136 on a two inch silicon wafer 138 (FIG. 8a). The wafer 138 was then etched using deep reactive ion etching (DRIE) (Laermer, et al., "Bosch Deep Silicon Etching: Improving Uniformity and Etch Rate for Advanced MEMS Applications," *Micro Electro Mechanical Systems*, Orlando, Fla., USA (Jan. 17-21, 1999)) in an inductively coupled plasma (ICP) reactor to etch deep vertical holes 140. The deep silicon etch was stopped after the holes 140 reached approximately 200 μm deep into the silicon substrate 138 (FIG. 8b). The photoresist 134 was removed, and a second photolithography step was used to pattern the remaining $SiO_2$ layer 136 into circles concentric to the holes, thus leaving ring shaped oxide masks 134 surrounding the holes (FIG. 8c). The photoresist 134 was then removed and the wafer 138 was again deep silicon etched, while simultaneously the holes 140 were etched completely through the wafer 138 (inside the $SiO_2$ ring) and the silicon was etched around the $SiO_2$ ring 138 leaving a cylinder 142 (FIG. 8d). The resulting tubes were 150 μm in height, with an outer diameter of 80 μm, an inner diameter of 40 μm, and a tube center-to-center spacing of 300 μm.

EXAMPLE 5

Micromold Fabrication of Metal Microtubes

Hollow metal microtubes were prepared without dry silicon etching, using a thick, photo-defined mold of epoxy. The sequences are illustrated in FIGS. 9a-e. First, a thick layer of SU-8 epoxy 144 was spin cast onto a silicon or glass substrate 146 that had been coated with 30 nm of titanium 148, the sacrificial layer. Arrays of cylindrical holes 149 were then photolithographically defined through an epoxy layer 144, typically 150 μm thick (FIG. 9a). The sacrificial layer 148 at the bottom of the cylindrical holes 149 then was partially removed using a wet etching solution containing hydrofluoric acid and water (FIG. 9b). A seed layer of Ti/Cu/Ti (30 nm/200 nm/30 nm) 139 was then conformally DC sputter-deposited onto the upper surface of the epoxy mold and onto the sidewalls of the cylindrical holes 149 (FIG. 9c). As shown in FIG. 9c, the seed layer 139 was electrically isolated from the substrate 146. Subsequently, NiFe 145 was electroplated onto the seed layer 139 (FIG. 9d), and the epoxy 144, the substrate 146, and the sacrificial layer 148 were removed, leaving the electroplated structure (microtubes) consisting of the Ti/Cu/Ti seed layer 139 and the NiFe layer 145 (FIG. 9e). The resulting microtubes are 200 μm in height with an outer diameter of 80 μm, an inner diameter of 60 μm, and a tube center-to-center spacing of 150 μm. The holes in the interior of the microtubes extend through the base metal supporting the tubes.

EXAMPLE 6

Micromold Fabrication of Tapered Microneedles

A micromold having tapered walls was fabricated by molding a preexisting 3-D array of microneedles, i.e. the mold-insert, and subsequently removing the mold insert. The micromold was then surface plated in a manner similar to that for the microtubes described in Example 5. The fabrication sequence is illustrated in FIGS. 10a-d.

First, an array of solid silicon microneedles 50 were prepared as described in Henry, et al., "Micromachined Needles for the Transdermal Delivery of Drugs," *Micro Electro Mechanical Systems*, Heidelberg, Germany, pp. 494-98 (Jan. 26-29, 1998). Then, a layer of epoxy 52 (SU-8) was spin cast onto the microneedle array to completely blanket the array (FIG. 10a). The epoxy 52 settled during pre-bake to create a planar surface above the tips of the microneedles 50. The epoxy 52 was then fully pre-baked, photolithographically cross-linked, and post-baked.

Then, the upper surface of the epoxy 52 was etched away using an $O_2/CHF_3$ plasma until approximately 1 to 2 μm of the needle tips 51 were exposed, protruding from the epoxy 52 (FIG. 10b). The silicon was then selectively removed by using a $SF_6$ plasma (FIG. 10c). The remaining epoxy mold 52 provided a negative of the microneedles with a small diameter hole where the tip of the silicon needle protruded. After the removal of the silicon, a seed layer of Ti—Cu—Ti 54 was conformally sputter-deposited onto the top and sidewalls of the epoxy micromold 52. Following the same process sequence as described in Example 5, NiFe 55 was then electroplated onto the seed layer 54. Finally, the epoxy 52 was removed using an $O_2/CHF_3$ plasma, leaving a released structure of hollow metal microneedles 56 formed of NiFe 55 layer and Ti—Cu—Ti 54 seed layer (FIG. 10d). The microneedles were made in a 20×20 array, and were 150 µm in height with a base diameter of 80 µm, a tip diameter of 10 µm, and a needle-to-needle spacing of 150 µm.

Micromold-based microneedles also have been successfully manufactured using a process in which the epoxy mold material was replaced with PDMS. In this case, it was possible to remove the mold from the mold insert, as well as the microneedles from the mold, using only physical techniques such as peeling. This approach advantageously requires no dry etching and allows one to reuse both the mold and the mold insert.

EXAMPLE 7

Micromold Fabrication of Tapered Microneedles Using Laser-Formed Molds

Figure 11A:
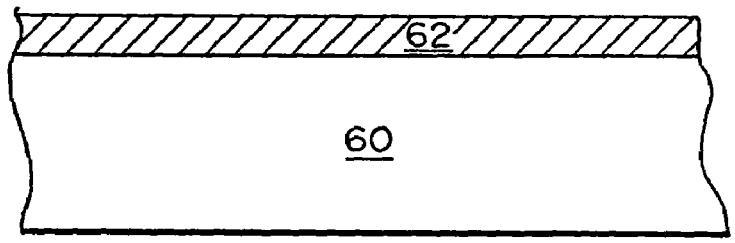
FIGS. 11a-d are side cross-sectional views illustrating a method for making tapered microneedles using laser-formed molds.
Figure 11B:
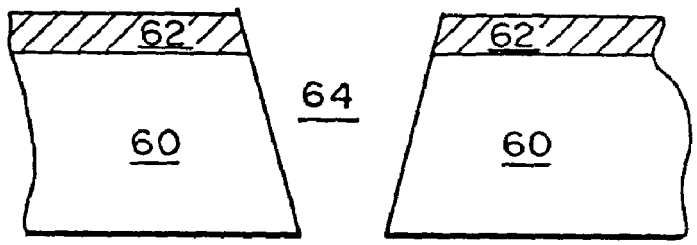
Figure 11C:
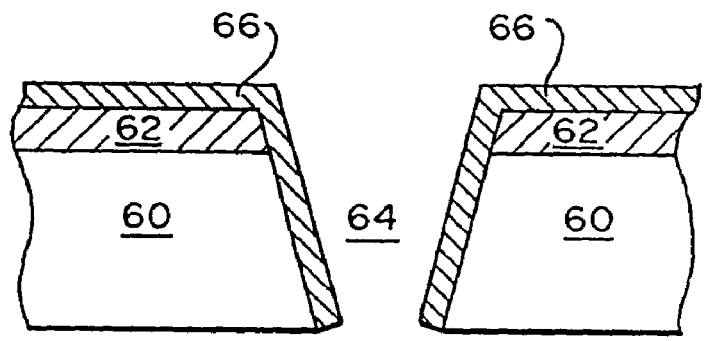
Figure 11D:
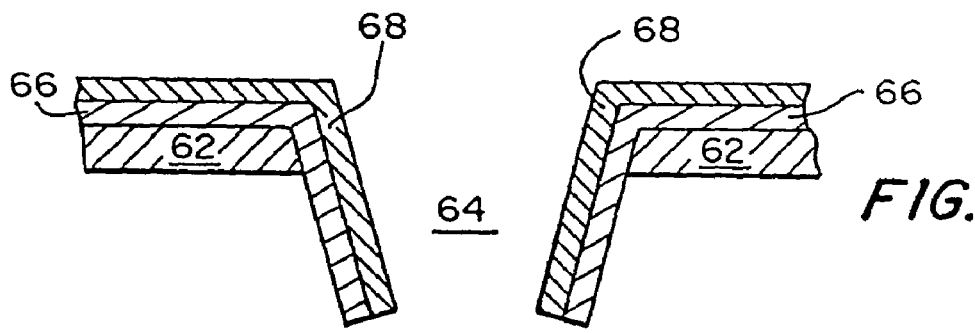

A micromold having tapered walls was fabricated by use of laser ablation techniques, as shown in FIGS. 11a-d. A laser-ablatable polymer sheet 60 such as KAPTON™ polyimide approximately 150 microns in thickness was optionally laminated to a thin (10-30 µm) metal sheet 62 such as titanium (FIG. 11a). A tapered hole 64 was formed in the metal/polymer laminate 60/62 using a laser technique such as excimer laser ablation (FIG. 11b). The entry hole of the laser spot was on the metal side 62, and a through hole was made through both the metal sheet and the polymer film. The through hole 64 was tapered in combination with either defocusing or appropriate substrate motion to create a taper such that the wide end of the hole 64 (typically 40-50 µm) was on the metal side 62 and the narrow end of the hole 64 (typically 10-20 µm) was on the polymer 60 side. A thin layer of metal 66, e.g. titanium, of thickness 0.1 micron was then deposited, e.g., using a sputter-deposition technique, in such a way that the metal 66 deposited on the metal film side and coated the polymer sidewalls, but did not coat the polymer 60 side of the laminate (FIG. 11c). Electrodeposition of metal 68, e.g., gold, to a thickness of 1 to 5 µm was then performed on the titanium-coated metal surface 66, and polymer sidewalls curved section of 60 next to 64. Finally, the polymer 60 was removed, using e.g. an oxygen plasma, to form the completed microneedles (FIG. 11d).

Alternate polymer removal methods, such as thermal, solvent, aqueous, or photo-degradation followed by solvent or aqueous removal, are also possible if the polymer material is chosen appropriately (e.g., a photoresist resin).

EXAMPLE 8

Formation of Microneedles by Embossing

Figure 12A:
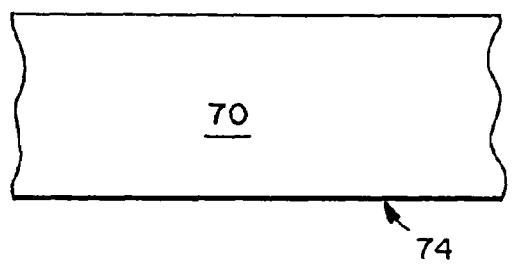
FIGS. 12a-f are side cross-sectional views illustrating a second method for making tapered microneedles using laser-formed molds.
Figure 12B:
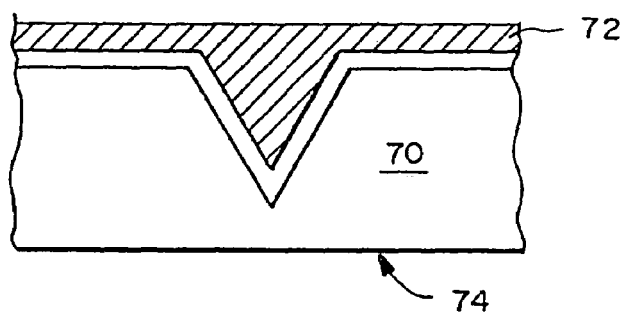
Figure 12C:
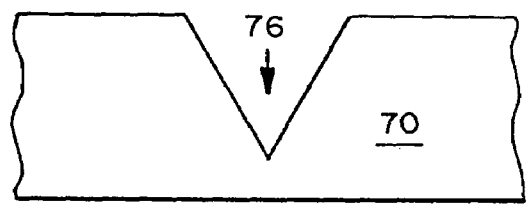
Figure 12D:
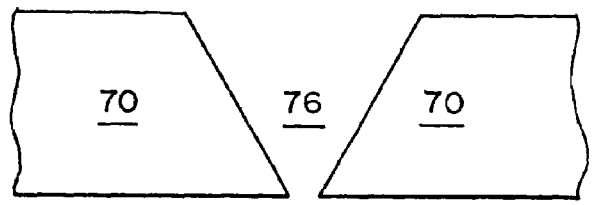
Figure 12E:
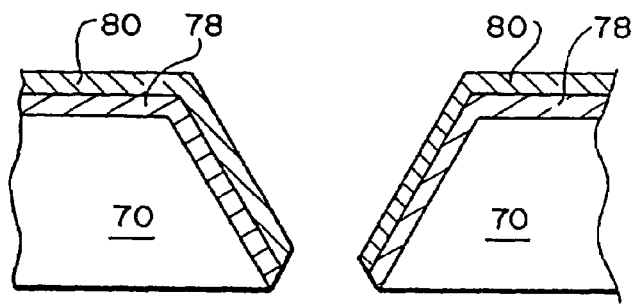
Figure 12F:
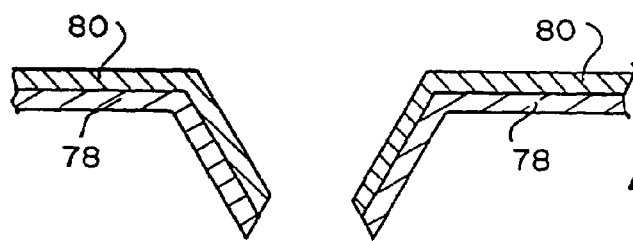

Formation of a microneedle by embossing is shown in FIGS. 12a-f. A polymeric layer 70 (FIG. 12a) is embossed by a solid microneedle or microneedle array 72 (FIG. 12b). The array 72 is removed (FIG. 12c), and the layer 70 is etched from the non-embossed side 74 until the embossed cavity 76 is exposed (FIG. 12d). A metallic layer 78 is then deposited on the embossed side and the sidewalls, but not on the non-embossed side 74 (FIG. 12e). This layer 78 is optionally thickened by electrodeposition of an additional metal layer 80 on top of it (FIG. 12e). The polymer layer 70 is then removed to form the microneedles 78/80 (FIG. 12f).

Publications cited herein and the material for which they are cited are specifically incorporated by reference. Nothing herein is to be construed as an admission that the invention is not entitled to antedate such disclosure by virtue of prior invention.

Modifications and variations of the methods and devices described herein will be obvious to those skilled in the art from the foregoing detailed description. Such modifications and variations are intended to come within the scope of the appended claims.

We claim:

1. A device for collecting a sample of a biological fluid comprising:
   one or more hollow or porous microneedles, each having a base end and a tip;
   a substrate to which the base end is attached or integrated; and
   at least one collection chamber suitable for collecting said sample of said biological fluid, said collection chamber selectably in fluid communication with the base end, and wherein said collection chamber comprises a one-way valve and an upper portion which is formed of a deformable material.

2. A device for collecting a sample of a biological fluid comprising:
   one or more hollow or porous microneedles, each having a base end and a tip;
   a substrate to which the base end is attached or integrated; and
   at least one collection chamber suitable for collecting said sample of said biological fluid, wherein said collection chamber is selectably in fluid communication with the base end, and comprises a plurality of compartments.

3. The device of claim 2, further comprising a means for inducing transport of a biological fluid or component thereof into the collection chamber.

4. The device of claim 3 wherein the pressure within the collection chamber can selectively be reduced.

5. The device of claim 4 wherein the pressure reduction is induced by expanding the internal volume of the collection chamber.

6. The device of claim 5 wherein the collection chamber is a standard or Luer-lock syringe.

7. The device of claim 3 wherein the collection chamber comprises an upper portion which is formed of a material which is deformable.

8. The device of claim 7 wherein the collection chamber comprises a one-way valve.

9. The device of claim 4 wherein the means for inducing transport comprises a plunger movably secured to the substrate, wherein the plunger can deform the collection chamber.

10. The device of claim 2, comprising a three dimensional array of microneedles.

11. The device of claim 2, further comprising an adhesive material for securing the device to a biological barrier surface during fluid withdrawal or sensing.

12. The device of claim 2, further comprising a means for controlling flow through the microneedle.

13. The device of claim 12 wherein the means for controlling flow is a fracturable or removable barrier which is interposed between the collection chamber and base of the microneedle.

14. The device of claim 2, further comprising a sensor in communication with the collection chamber.

15. The device of claim 2, wherein the collection chamber is adapted to receive and use glucose strips.

16. The device of claim 2, wherein the microneedle is hollow and comprises at least one opening in the side of the microneedle.

17. The device of claim 2, wherein the microneedle has a hollow bore containing a material to modulate the flow of biological fluid through the microneedles into the collection chamber.

18. The device of claim 2, wherein the microneedle is hollow.

19. The device of claim 2, wherein the microneedle is perpendicular to a surface of the substrate.

20. The device of claim 2, wherein the microneedle has a diameter between about 40 and 120 μm.

21. A device for collecting a sample of a biological fluid comprising:
one or more hollow or porous microneedles, each having a base end and a tip;
a substrate to which the base end is attached or integrated;
at least one collection chamber suitable for collecting said sample of said biological fluid, said collection chamber selectably in fluid communication with the base end; and
a fracturable or removable barrier for controlling flow through the microneedle, said barrier interposed between the collection chamber and base of the microneedle.

22. A device for collecting a sample of a biological fluid comprising:
one or more hollow or porous microneedles, each having a base end and a tip;
a substrate to which the base end is attached or integrated; and
at least one collection chamber suitable for collecting said sample of said biological fluid, said collection chamber selectably in fluid communication with the base end,
wherein the one or more microneedles has a hollow bore containing a material to modulate the flow of biological fluid through the microneedles into the collection chamber.

23. The device of any one of claims 1-22, wherein the one or more microneedles each has a length between about 500 μm and 1 mm and a width between about 1 μm and 500 μm.

24. A device for collecting a sample of a biological fluid comprising:
one or more hollow or porous microneedles, each having a base end and a tip, a length between 500 μm and 1 mm and a width between about 1 μm and 500 μm, and comprising a metal;
a substrate to which the base end is attached or integrated; and
at least one collection chamber suitable for collecting said sample of said biological fluid, said collection chamber selectably in fluid communication with the base end.

25. A method for collecting a sample of a biological fluid or analyte therein, comprising the steps:
providing the device of any one of claims 1-24;
inserting said one or more microneedles of the device into a biological barrier comprising biological fluid; and
triggering the transport of a quantity of the biological fluid or analyte therein through said one or more microneedles and into the collection chamber.

26. The method of claim 25, wherein triggering the transport is effected by capillary action, diffusion, mechanical pumps, electroosmosis, electrophoresis, convection, or combinations thereof.

27. The method of claim 25, wherein triggering the transport is effected by a pressure gradient in which the pressure within the microneedles and/or collection chamber is less than the pressure of the biological fluid adjacent the tip of the microneedle.

28. The method of claim 25 wherein the analyte to be collected or sensed is selected from the group consisting of glucose, cholesterol, bilirubin, creatine, metabolic enzymes, hemoglobin, heparin, clotting factors, uric acid, tumor antigens, reproductive hormones, oxygen, pH, alcohol, tobacco metabolites, and illegal drugs.

29. The method of claim 25, wherein the analyte is glucose, and wherein the biological barrier is human skin.

30. The device of claim 24, wherein the microneedle consists essentially of a metal.

31. A device for sensing an analyte in a biological fluid comprising:
one or more microneedles, each having a base end and a tip, a length between about 500 μm and 1 mm and a width between about 1 μm and 500 μm, and comprising a metal;
a substrate to which the base of the microneedle is attached or integrated; and
at least one sensor which is selectably in fluid communication with the microneedle.

32. A device for sensing an analyte in a biological fluid comprising:
one or more microneedles, each having a base end and a tip;
a substrate to which the base of the microneedle is attached or integrated; and
at least one sensor which is selectably in fluid communication with the microneedle,
wherein the one or more microneedles has a hollow bore containing a material to modulate the flow of biological fluid through the microneedles into a collection chamber.

33. The device of claim 32, wherein the sensor comprises:
a chemical or biochemical agent that react with the analyte, and
electrochemical or optical transducers which measure the reaction of the agent and the analyte.

34. The device of claim 33 wherein the agent is an enzyme selected from the croup consisting of glucose oxidase, glucose dehydrogenase, and combinations thereof.

35. The device of claim 32, further comprising an electronics package in communication with the sensor.

36. The device of claim 32, wherein the microneedle comprises a metal.

37. The device of claim 36, wherein the microneedle consists essentially of a metal.

38. The device of claim 32, wherein the microneedle is hollow.

39. The device of claim 32, wherein the microneedle is perpendicular to a surface of the substrate.

40. A device for sensing an analyte in a biological fluid comprising:
one or more microneedles, each having a base end and a tip; and
a substrate to which the base of the microneedle is attached or integrated, wherein at least one of the microneedles is or comprises a sensor, and wherein the one or more microneedles has a hollow bore containing a material to modulate the flow of biological fluid through the microneedles into a collection chamber.

41. The device of claim 40, wherein the sensor comprises:
a chemical or biochemical agent that reacts with the analyte, and
electrochemical or optical transducers which measure the reaction of the agent and the analyte.

42. The device of claim 40, further comprising an electronics package in communication with the sensor.

43. A method for sensing an analyte in a biological fluid, comprising the steps:
providing the device of claim 31, 32, or 40;
inserting said one or more microneedles into a biological barrier comprising said biological fluid which contains said analyte; and
contacting the sensor with the biological fluid, thereby sensing the analyte.

44. The method of claim 43 wherein the device further comprises:
at least one collection chamber which is selectably in fluid connection with the base end of the microneedle, and
a means for inducing transport of the biological fluid or the analyte therein into the collection chamber,
wherein, after the microneedles are inserted, the means for inducing is triggered to draw the biological fluid or the analyte therein through the microneedles and into the collection chamber.

45. The method of claim 44 wherein the means for inducing utilizes a pressure gradient in which the pressure within the microneedles and for collection chamber is less than the pressure of the biological fluid adjacent the tip of the microneedle.

46. The method of claim 45 wherein the pressure gradient is created by increasing the volume within the collection chamber.

47. The method of claim 43 wherein the analyte to be collected or sensed is selected from the group consisting of glucose, cholesterol, bilirubin, creatine, metabolic enzymes, hemoglobin, heparin, clotting factors, uric acid, tumor antigens, reproductive hormones, oxygen, pH, alcohol, tobacco metabolites, and illegal drugs.

48. The method of claim 43, wherein the analyte is glucose, and wherein the biological barrier is human skin.

* * * * *

UNITED STATES PATENT AND TRADEMARK OFFICE
CERTIFICATE OF CORRECTION

PATENT NO. : 7,344,499 B1
APPLICATION NO. : 09/453109
DATED : March 18, 2008
INVENTOR(S) : Prausnitz et al.

Page 1 of 1

It is certified that error appears in the above-identified patent and that said Letters Patent is hereby corrected as shown below:

In the Claims:

Claim 7, col. 24, line 46, delete "3" and instead insert --4--;

Claim 23, col. 25, line 42, delete "1-22" and instead insert --1, 2, 21, and 22--;

Claim 25, col. 25, line 58, delete "1-24" and instead insert --1, 2, 21, 22 and 24--; and Claim 34, col. 26, line 46, delete "croup" and instead insert --group--.

Signed and Sealed this

Seventeenth Day of March, 2009

JOHN DOLL
*Acting Director of the United States Patent and Trademark Office*